(12) United States Patent
Burg

(10) Patent No.: US 10,948,352 B2
(45) Date of Patent: Mar. 16, 2021

(54) PRECISION LUXMETER METHODS FOR DIGITAL CAMERAS TO QUANTIFY COLORS IN UNCONTROLLED LIGHTING ENVIRONMENTS

(71) Applicant: HEALTHY.IO LTD., Tel Aviv-Jaffa (IL)

(72) Inventor: Bernard Burg, Menlo Park, CA (US)

(73) Assignee: HEALTHY.IO LTD., Tel Aviv-Jaffa (IL)

(*) Notice: Subject to any disclaimer, the term of this patent is extended or adjusted under 35 U.S.C. 154(b) by 149 days.

(21) Appl. No.: 15/865,238

(22) Filed: Jan. 8, 2018

(65) Prior Publication Data

US 2018/0252585 A1 Sep. 6, 2018

Related U.S. Application Data

(63) Continuation of application No. 14/827,312, filed on Aug. 15, 2015, now Pat. No. 9,863,811.
(Continued)

(51) Int. Cl.
*G06K 9/00* (2006.01)
*G01J 3/52* (2006.01)
(Continued)

(52) U.S. Cl.
CPC . *G01J 3/52* (2013.01); *G01J 1/42* (2013.01); *G01J 1/4204* (2013.01); *G01J 3/50* (2013.01);
(Continued)

(58) Field of Classification Search
CPC ...... G01J 3/52; G01J 3/50; G01J 3/524; G01J 3/0272; G01J 1/42; G01J 1/4204; G01J 1/08; G06T 7/90; G06T 2207/10024; G06T 2207/30004; G01N 33/487; G01N 21/78; G01N 21/8483; G01N 2201/129; H04N 9/735
See application file for complete search history.

(56) References Cited

U.S. PATENT DOCUMENTS 6,122,042 A * 9/2000 Wunderman ............ A61B 1/05
356/343
9,285,323 B2 * 3/2016 Burg ...................... G01N 21/78
(Continued)

*Primary Examiner* — Shefali D Goradia
(74) *Attorney, Agent, or Firm* — Finnegan, Henderson, Farabow, Garrett & Dunner, LLP

(57) ABSTRACT

In one embodiment, a diagnostic system for biological samples is disclosed. The diagnostic system includes a diagnostic instrument, and a portable electronic device. The diagnostic instrument has a reference color bar and a plurality of chemical test pads to receive a biological sample. The portable electronic device includes a digital camera to capture a digital image of the diagnostic instrument in uncontrolled lightning environments, a sensor to capture illuminance of a surface of the diagnostic instrument, a processor coupled to the digital camera and sensor to receive the digital image and the illuminance, and a storage device coupled to the processor. The storage device stores instructions for execution by the processor to process the digital image and the illuminance, to normalize colors of the plurality of chemical test pads and determine diagnostic test results in response to quantification of color changes in the chemical test pads.

18 Claims, 17 Drawing Sheets

Related U.S. Application Data

(60) Provisional application No. 62/038,155, filed on Aug. 15, 2014.

(51) Int. Cl.

| | | |
|---|---|---|
| *G01N 33/487* | (2006.01) | |
| *G01J 1/42* | (2006.01) | |
| *G01J 3/50* | (2006.01) | |
| *H04N 9/73* | (2006.01) | |
| *G06T 7/90* | (2017.01) | |
| *G01J 1/08* | (2006.01) | |
| *G01J 3/02* | (2006.01) | |
| *G01N 21/78* | (2006.01) | |
| *G01N 21/84* | (2006.01) | |

(52) U.S. Cl.
CPC ............... *G01J 3/505* (2013.01); *G01J 3/524* (2013.01); *G01N 33/487* (2013.01); *G06T 7/90* (2017.01); *H04N 9/735* (2013.01); *G01J 1/08* (2013.01); *G01J 3/0272* (2013.01); *G01N 21/78* (2013.01); *G01N 21/8483* (2013.01); *G01N 2201/129* (2013.01); *G06T 2207/10024* (2013.01); *G06T 2207/30004* (2013.01)

(56) References Cited

U.S. PATENT DOCUMENTS

| | | | | |
|---|---|---|---|---|
| 9,528,941 B2* | 12/2016 | Burg | ...................... | G01N 21/78 |
| 9,600,878 B2* | 3/2017 | Tsai | ................... | G01N 21/8483 |
| 9,972,077 B2* | 5/2018 | Adiri | ..................... | G06K 9/2027 |
| 2003/0016865 A1* | 1/2003 | Lopez | .................. | H04N 1/6086 |
| | | | | 382/165 |
| 2012/0063652 A1* | 3/2012 | Chen | ................... | G01N 21/274 |
| | | | | 382/128 |

\* cited by examiner

PRECISION LUXMETER METHODS FOR DIGITAL CAMERAS TO QUANTIFY COLORS IN UNCONTROLLED LIGHTING ENVIRONMENTS

CROSS REFERENCE TO RELATED APPLICATIONS

This application is a continuation and claims the benefit of U.S. patent application Ser. No. 14/827,312 entitled PRECISION LUXMETER METHODS WITH A DIGITAL CAMERA TO QUANTIFY COLORS IN UNCONTROLLED LIGHTING ENVIRONMENTS filed on Aug. 15, 2015 by inventor Bernard Burg. U.S. patent application Ser. No. 14/827,312 claims the benefit of U.S. provisional patent application Ser. No. 62/038,155 entitled PRECISION LUXMETER METHODS WITH A DIGITAL CAMERA TO QUANTIFY COLORS IN UNCONTROLLED LIGHTING ENVIRONMENTS filed on Aug. 15, 2014 by inventor Bernard Burg.

This application is related to U.S. patent application Ser. No. 14/633,518 entitled QUANTIFYING COLOR CHANGES OF CHEMICAL TEST PADS INDUCED BY SPECIFIC CONCENTRATIONS OF BIOLOGICAL ANALYTES UNDER DIFFERENT LIGHTING CONDITIONS filed on Feb. 27, 2015 by Bernard Burg et al. which is incorporated herein by reference for all purposes. U.S. patent application Ser. No. 14/633,518 claims priority to provisional patent application No. 61/948,536 entitled APPARATUS FOR DETERMINING ANALYTE CONCENTRATION BY QUANTIFYING AND INTERPRETING COLOR INFORMATION CAPTURED IN A CONTINUOUS OR PERIODIC MANNER filed on Mar. 5, 2014 by Bernard Burg et al. (hereinafter Burg '536), which is incorporated herein by reference for all purposes.

This application is also related to International Patent Ap. No. PCT/US2013/035397, Publication No. WO 2014025415 A2, filed on Aug. 5, 2013 by Bernard Burg et al. (hereinafter Burg '397), and U.S. patent application Ser. No. 14/419,939 entitled METHOD AND APPARATUS FOR PERFORMING AND QUANTIFYING COLOR CHANGES INDUCED BY SPECIFIC CONCENTRATIONS OF BIOLOGICAL ANALYTES IN AN AUTOMATICALLY CALIBRATED ENVIRONMENT filed Feb. 6, 2015, both of which are incorporated herein by reference for all purposes. PCT Application No. PCT/US2013/035397 claims the benefit of U.S. provisional patent application No. 61/680,842 entitled MULTI-ANALYTE RAPID DIAGNOSTIC TEST AND METHOD OF USE filed on Aug. 8, 2012, by inventors Bernard Burg et al which is also incorporated herein by reference for all purposes.

FIELD

The invention relates generally to systems and methods for measuring photometric units in uncontrolled lighting environments with digital cameras.

BACKGROUND

Illuminance $E_v$ is the area density of luminous flux received by an illuminated body, integrated with all wavelengths and all directions. Illuminance is used to gauge the amount of light incident on a surface. A unit of illuminance is a lux (lx), lumens per square meter. Another unit of illuminance is foot candles. Illuminance on a surface area is luminous flux per area defined by the equation:

$$E_v = \frac{\text{luminous flux}}{\text{area}} = \frac{d\Phi_v}{dA}$$

The spectral illuminance $E_v(\lambda)$ is defined by the illuminance per unit wavelength interval at the wavelength $\lambda$. Spectral illuminance $E_v(\lambda)$ is related to the illuminance $E_v$ by the equation $$E_v = \int_0^\infty E_v(\lambda) d\lambda$$

A device or application that measures illuminance is referred to as a luxmeter. Luxmeter software applications that measure illuminance are available for use with portable electronic devices that include a digital camera. The luxmeter software application is executed by a processor and the operating system software (e.g., APPLE iOS and GOOGLE Android) of the portable electronic device. The accuracy of the luxmeter software applications is often limited by the sensor and digital camera used in the portable electronic device. In addition, OS manufacturers may only provide incomplete application programming interfaces (API) to these sensors, or prohibit direct access by other applications to these sensors. Consequently, luxmeter applications typically have limited access to metadata of the digital pictures taken with a digital camera, if available. Typical metadata parameters produced by portable electronic device cameras that are associated with digital photographs are:
ExposureTime;
ShutterSpeedValue;
FNumber;
ApertureValue;
BrightnessValue;
ISOSpeedRatings;

These metadata parameters are sometimes stored in registers as register settings. The metadata parameters ExposureTime, ShutterSpeedValue, FNumber, and ApertureValue are well defined because they follow standard photographic values. The parameter ExposureTime is related to the parameter ShutterSpeedValue through the mathematical equation:

$$ExposureTime = \frac{1}{2^{ShutterSpeedValue}}$$

The parameter FNumber is related to ApertureValue through the mathematical equation:

$$FNumber = \sqrt{2^{ApertureValue}}$$

The metadata parameter values of BrightnessValue and ISOSpeedRatings vary from camera to camera, such that they are difficult to use for a luxmeter application. As a consequence, luxmeters in applications are quite approximate or require an external calibration before use.

A number of references disclosing measurement of illuminance conditions were developed during the argentic film era, such as U.S. Pat. Nos. 3,972,626, and 3,973,266, when film based cameras were used to capture photos. Digital cameras revolutionized the structure of cameras, capturing pixels of images and storing them into flash memory. A number of analog optical mechanisms were replaced with digital computations. Accordingly, some inventions disclosed in patents, such as U.S. Pat. No. 5,737,648, were no longer relevant. New illuminance measurement methods were introduced for digital cameras.

U.S. Pat. No. 7,071,456 discloses a camera illuminance sensor to set lighting levels of I/O systems, such as keypads, and backlights for adjustable displays. U.S. Pat. App. Pub. No. 2012/0236173 similarly discloses adapting a camera user interface to environmental conditions. U.S. Pat. App. Pub. No. 2012/0236173 discloses use of a plurality of sensors to allow corrections for underwater conditions such as very cold conditions, very bright conditions, and very dark conditions. U.S. Pat. App. Pub. No. 2012/0236173 discloses addressing illuminance conditions of extreme brightness and extreme darkness, but does not make precise illuminance measurements.

U.S. Pat. No. 7,629,998 and U.S. Pat. App. Pub. No. 2007/0002143 disclose a method and apparatus for measuring the performance of a camera, including illuminance. A test environment is disclosed to better comprehend and verify the specifications of a camera and test their fitness. The disclosed approach to measure illuminance requires that additional sensors be used for the test environment.

U.S. Pat. App. Pub. No. 2001/0007470 entitled MEASUREMENT OF ILLUMINANCE CONDITIONS uses external light emitting diodes (LEDs), as well as color filters and photo sensors to measure illuminance. The LEDs are used to control the lighting conditions. The intensity of each main color in the illuminance light is measured by dedicated photosensors having corresponding color measurement bands. These color intensities are used to adjust signals originating from the charge coupled device (CCD) array of the photo image sensor. Using external light emitting diodes (LEDs) and color filters makes it more difficult to measure illuminance.

It is desirable to ease the measurement of illuminance so that it can be readily used.

SUMMARY OF THE INVENTION

An illuminance model and additional measurements are introduced to increase the accuracy of illuminance measurements and to further improve color quantification in digital photographs captured with portable electronic device digital cameras, so they can be used with a medical device under different lighting environments with unknown illuminance.

DETAILED DESCRIPTION

In the following detailed description, numerous specific details are set forth in order to provide a thorough understanding. However, it will be obvious to one skilled in the art that the embodiments may be practiced without these specific details. In other instances well known methods, procedures, modules and components may not have been described in detail so as not to unnecessarily obscure aspects of the embodiments.

The embodiments include a method, apparatus and system for color quantification under various lighting conditions. The color quantification can be used to detect and quantify specific concentrations of biological analytes indicated by a diagnostic test device.

Principle of Illuminance Learning Algorithm

Figure 12:
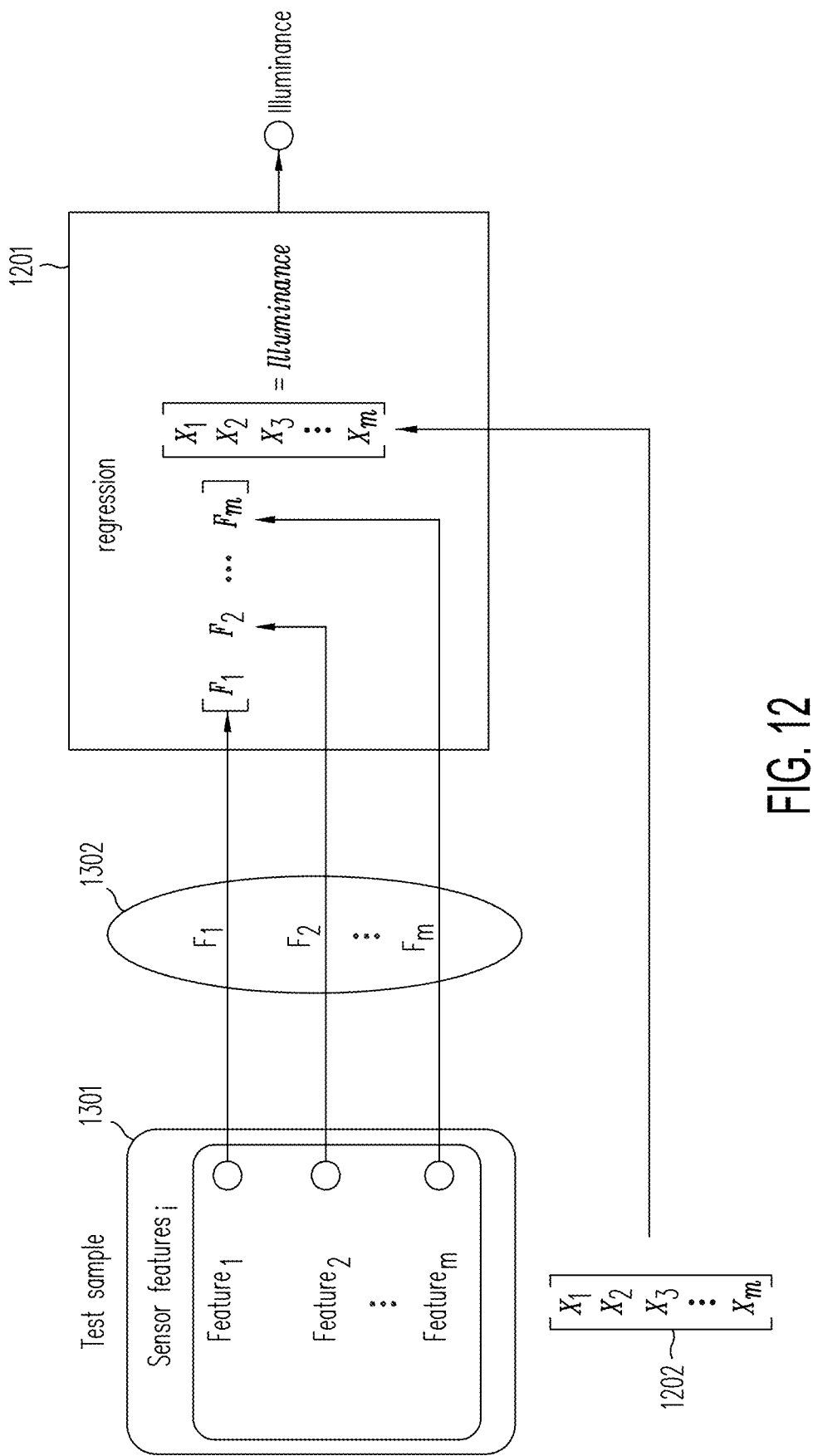
FIG. 12 illustrates the block diagram of the color quantification model during the test or measurement phase.

FIG. 12 shows a model for estimating illuminance (referred to as an illuminance model). The illuminance model is a regression model that is initially trained in a learning or training phase/mode. Once trained, the illuminance model in a testing mode can estimate the illuminance of a scene where digital photographs are captured.

Figure 11:
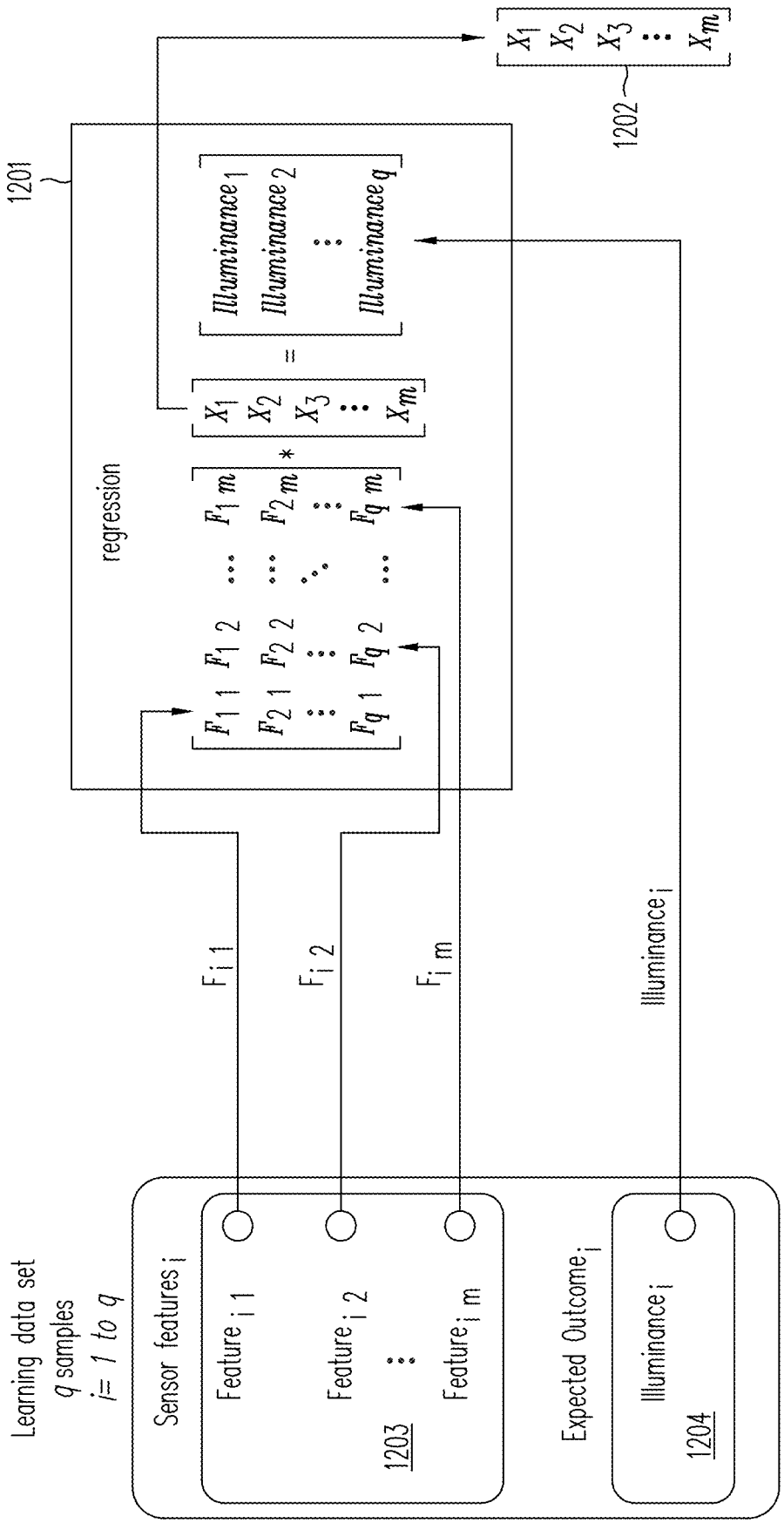
FIG. 11 illustrates a block diagram of the color quantification model during the learning phase.

FIG. 11 illustrates the illuminance model in the learning or training phase/mode to determine a best set of m parameters $X_1$ through $X_m$ of a parameter vector X for estimating illuminance. During the learning phase for the illuminance model, a learning/training data set of q color samples is input to the illuminance model. A sensor of the digital camera captures the color samples and forms m sensor features $F_{im}$ 1203 for each sample i. Accordingly, each sample i can be described by a line or row vector $M_i$ as follows:

$$M_i = [F_{i\,1}\,F_{i\,2}\,\ldots\,F_{i\,m}]$$

The vector $M_i$ has m features and represents the sensory input 1203 provided to the regression model 1201. There are q row vectors $M_i$, one for each sample.

In the learning/training phase, there is an expected outcome to the illuminance, illuminance$_i$ 1204 for each sample i. During this learning phase, the variable Illuminance$_i$ 1204 is recorded along with the measurements of the sensor features $F_{im}$ 1203. The recorded illuminance$_i$ 1204 for each sample i forms an illuminance matrix I. The measurements of the sensor features $F_{im}$ 1203 for each sample i forms a sensor input matrix F.

The goal of learning phase is to find the best estimate of vector X 1202 for the regression algorithm 1201. The vector X 1202 is the best set of m parameters $X_1$ through $X_m$ for estimating illuminance. In transpose matrix form, the parameter vector X 1202 is $$X^T = [X_1\ X_2\ X_3 \ldots X_m]$$

The regression algorithm 1201 multiplies the sensor input matrix F with the parameter matrix X to determine the illuminance matrix I. In expanded form the regression algorithm 1201 performs the matrix operation of $$\begin{bmatrix} F_{11} & F_{12} & \ldots & F_{1m} \\ F_{21} & F_{22} & \ldots & F_{2m} \\ \vdots & \vdots & \ddots & \vdots \\ F_{q1} & F_{q2} & \ldots & F_{qm} \end{bmatrix} * \begin{bmatrix} X_1 \\ X_2 \\ X_3 \\ \vdots \\ X_m \end{bmatrix} = \begin{bmatrix} \text{Illuminance}_1 \\ \text{Illuminance}_2 \\ \vdots \\ \text{Illuminance}_q \end{bmatrix}$$

Knowing each value of the F matrix and each value of the illuminance matrix I, the m parameters $X_1$ through $X_m$ for the parameter matrix X can be determined. With the parameter matrix X determined, the illuminance model can then be used in a test mode/phase to determine illuminance.

FIG. 12 illustrates the test or measurement phase of the illuminance model. It is desirable to determine the illuminance, under which an image of a test sample was captured. The sensor includes a plurality of m sensor features Feature$_1$ through Feature$_M$ 1301. The sensor captures the test sample generating a measurement vector M 1302 with measurement features F1 through Fm. The vector M is represented in matrix form as follows:

$$M = [F_1\ F_2 \ldots F_m]$$

In the illuminance model, the vector M vector 1302 as well as the previously learned parameter X vector 1202, are provided to the regression algorithm 1201. In transpose form, the vector X vector 1202 is represented as follows $$X^T = [X_1\ X_2\ X_3 \ldots X_m]$$

With the measurement vector M and the parameter vector X, the illuminance model can predict the illuminance from the following matrix equation $$M*X = \text{Illuminance}$$

While the illuminance model is shown and described using a linear regression and linear equations, a non-linear regression and non-linear equations may be used to estimate illuminance.

Applications

Measuring with high accuracy the illuminance of a scene with a portable electronic device is one application. Camera metadata of a photograph are insufficient to accurately predict illuminance. In vector form, camera metadata generally provides:

$$M_{Meta\ i} = [\text{ExposureTime}_i\ \text{ShutterSpeed}_i\ F\text{Number}_i\ \text{Aperture}_i\ \text{Brightness}_i\ \text{IsoSpeedRating}_i].$$

Figure 14:
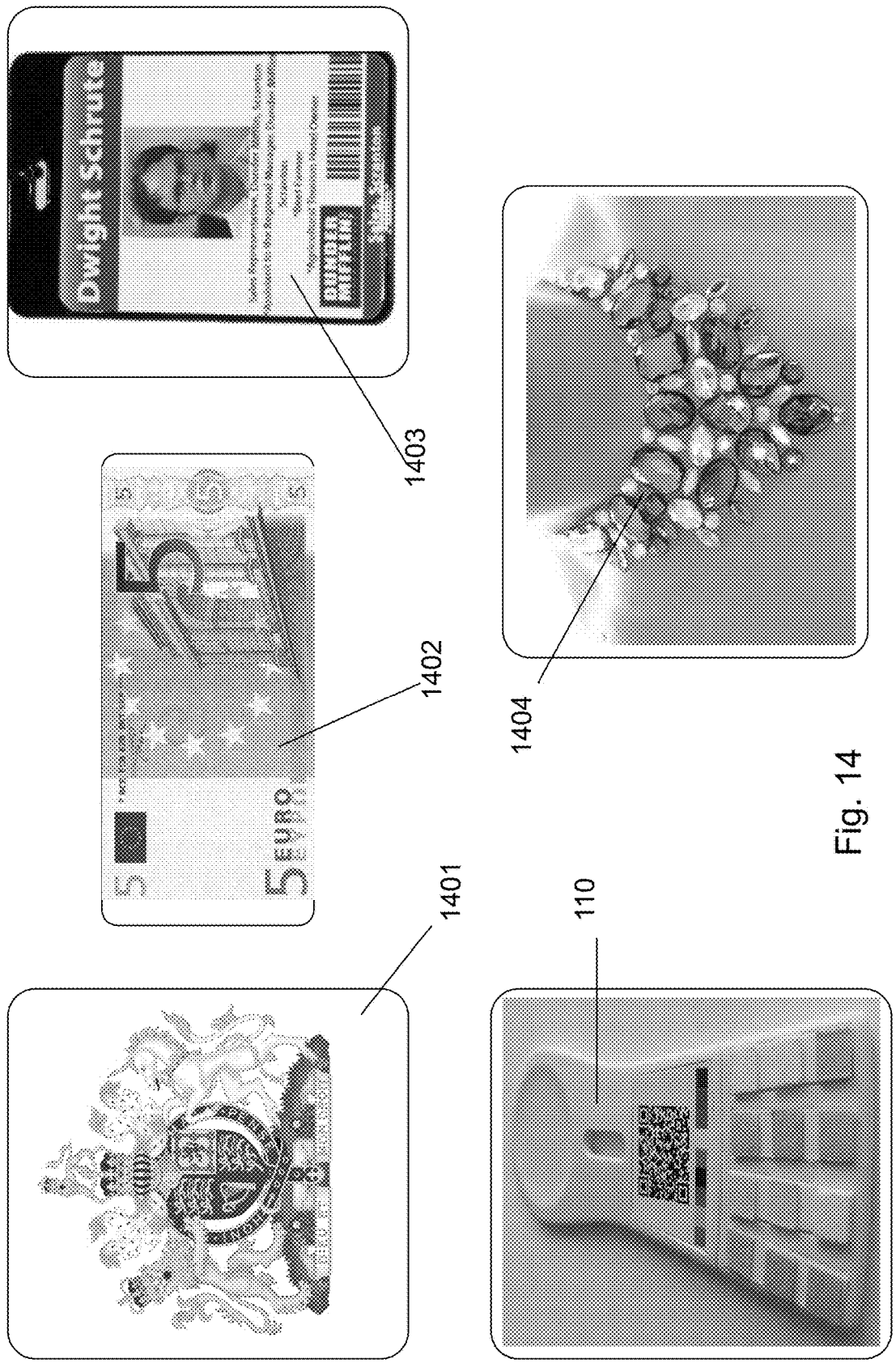
FIG. 14 illustrates a number of objects that may be used to increase the accuracy of the methods of lux measurements with a digital camera.

Referring now to FIG. 14, images of predetermined colored objects with different colors may be used to gain accuracy of lux measurements with a digital camera, some of which are commonly carried by users. For a baseline, the different colors of the predetermined colored object can be predetermined colors under known lighting conditions with known illuminances. Digital photos or images of the predetermined colored object can then be captured under unknown lighting conditions and unknown illuminances. A measure of illuminance for the digital photos captured under unknown lighting conditions can then be determined. The measure of illuminance can be used to more accurately extract colors and features from portions of a digital photograph or a colored object. It may be desirable to examine, authenticate, and/or validate the colored object or images of colored objects, persons, or parts thereof within a digital photograph. The analysis of the biological samples, such as blood and urine for example, is of great interest to determine concentrations of analytes as a function of color.

The predetermined colored object may be a colored seal 1401 for example. The predetermined colored object may be a colored bank note 1402 often found in purses, wallets, or pockets. The predetermined colored object may be a color identification (ID) badge or pass 1403 often worn on clothes or carried by a user. The predetermined colored object may be color jewelry 1404 that is worn by a user. The predetermined colored object may also be a special object dedicated to predetermined applications, such as a diagnostic instrument 110 or medical device. To improve lux measurements with a portable electronic device including a camera, it is desirable that the predetermined colored object contains multiple regions with diverse colors.

Figure 15:
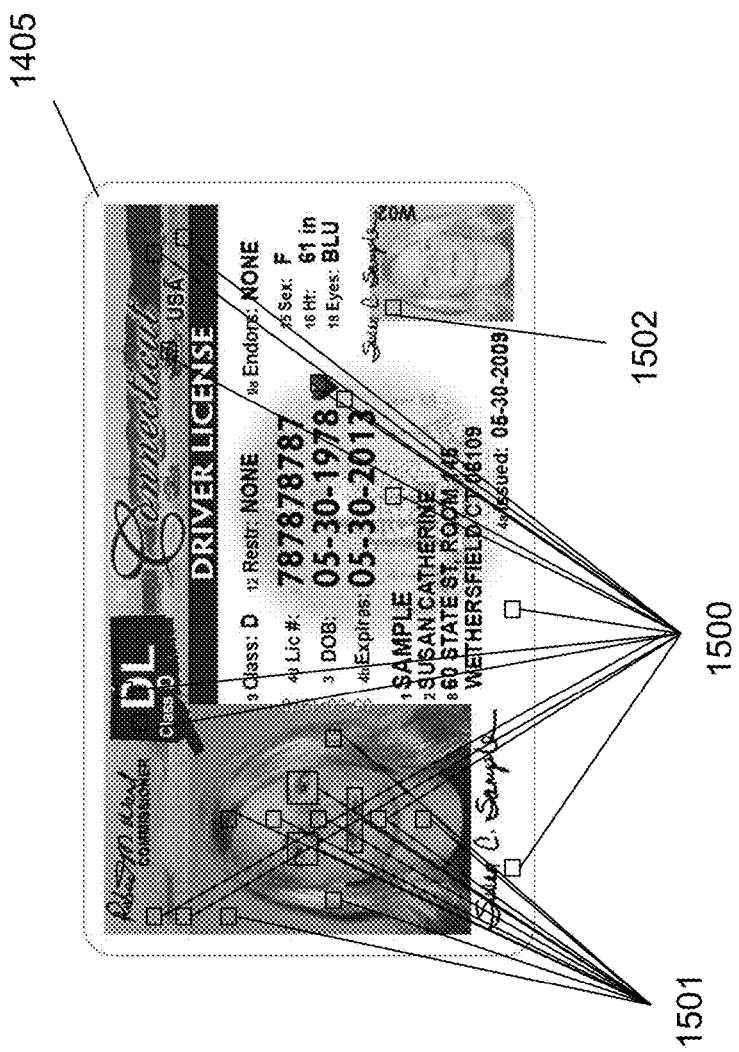
FIG. 15 illustrates an example of feature extraction using a driver license.

Referring now to FIG. 15, a state driver license 1405 is illustrated. The driver license 1405 may be another predetermined colored object that can be used to improve the accuracy of lux measurements obtained from digital photos taken with a digital camera. The state driver license 1405 includes a plurality of regions with diverse colors. An example of such regions is illustrated by points in the layout 1500 of the license, and points in the one or more pictures 1501-1502 of the driver license.

In this case, a template-based algorithm with predetermined knowledge of the drivers license extracts colors of features $F_1, F_2, \ldots F_m$ corresponding to the driver's license layout 1500. The color features can be arranged into a vector Mtemp as follows:

$$M\text{temp} = [F_1\ F_2 \ldots F_m]$$

A digital image of the license may be scanned to detect a feature and then extract the color of that feature. For example, a pink hued header background may be detected and the pink color extracted from the digital photograph. Clouds in the pink hued header background may be detected and the dark pink color extracted from the digital photograph. A blue state name in the header background may be scanned and detected. The blue color in the state name may be extracted for analysis. The color of the background detected in the driver license may be extracted.

A facial recognition algorithm extracts colors of the features in the driver's picture 1501. One feature in the picture, for example, may be the color of the eyes. The algorithm may scan for pictures of faces and detect the eyes of each face in a picture. The color of the eyes may be extracted. The color of the face/skin detected at different locations in the picture may be extracted. The color of hair at different locations detected in the picture may be extracted. The color of the background detected in the picture 1501 of the driver license may be extracted. A vector Mpic1 with these features $F_1'$ through $F_n'$ from the driver picture 1501 can be formed $$M\text{pic1} = [F_1'\ F_2' \ldots F_1'\ F_2' \ldots F_n']$$

If there is another picture, such as a second driver picture 1502, the same algorithm may be applied to extract color of features from the picture. Another vector Mpic2 with color of features $F_1''$ through $F_l''$ extracted from the driver picture 1502 can be formed $$Mpic2=[F''_1\ F''_2\ \ldots\ F''_l]$$

The simplest feature extraction analyzes the region and extracts its dominant color. For example, a dominant color may be defined as the median RGB color of the region.

A complete set of features extracted from the predetermined object can be formed into a merged vector M, including the metadata of the digital photo, as follows:

$$M=[M_{Meta}\ M_{temp}\ M_{pic1}\ M_{pic2}]$$

The features and colors of the diagnostic instrument 110 or medical device can be similarly extracted and merged into a vector for analysis. An ID tag on the instrument may provide the locations of the features to be extracted from the diagnostic instrument.

Figures 1A, 1B:
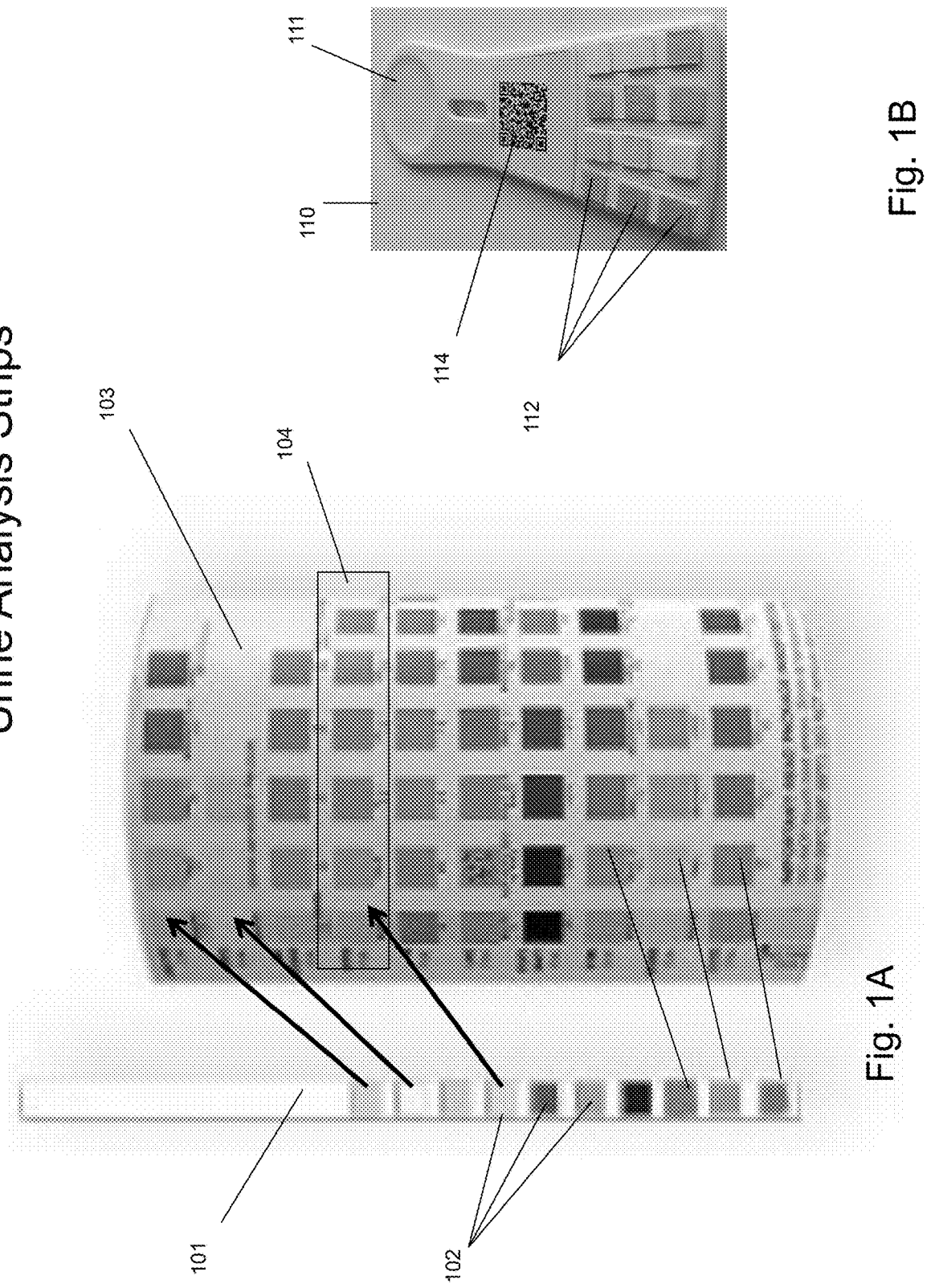
FIG. 1A illustrates a urine analysis test strip and an associated manufacturer interpretation color chart (MICC)
FIG. 1B illustrates a urine analysis paddle.

FIGS. 1A-1B illustrates a urine analysis test strip 101 and a urine analysis test paddle 110, for example. Accurate inference of colors of pixels in images captured by digital cameras has many practical applications. One such application is the analysis of urine with test strips and test paddles, where colors of chemical agents change depending on concentration of target substances in the urine samples. Other body fluids, such as blood, may be similarly analyzed with color representing the concentration of target substances in the biological samples.

Learning Illuminance

Figure 9:
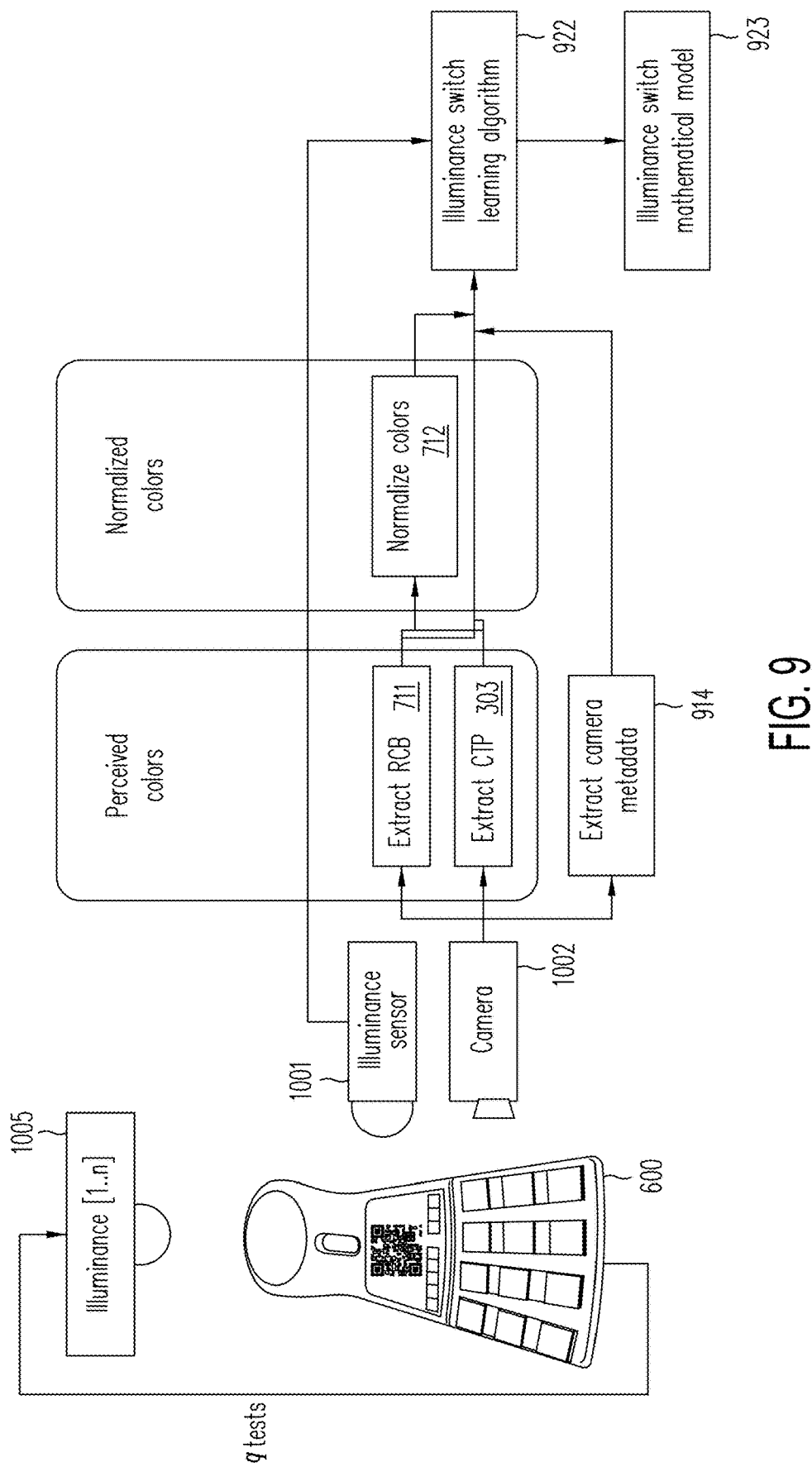
FIG. 9 illustrates a functional block diagram corresponding to the learning phase and the determination of the mathematical model of the illuminance switch by the learning algorithm of FIG. 8.

Reference is now made to FIG. 9. During the learning phase, numerous (e.g., hundreds) images are generated for each illuminance [1 . . . n], resulting in several (e.g., thousands) overall tests q. After all tests are performed, the learning algorithm determines the mathematical model capable of best predicting Illuminance$_x$, based on vector $M_x$.

The illuminance model is formed with a regression model, which is capable to classify the illuminance into n bins of illuminance values in response to the observation vector $M_t$. In the simple case of a linear regression, the illuminance model is trained with the parameter vector X, the transpose of which is as follows:

$$X^T=[X_1\ X_2\ X_3\ \ldots\ X_m]$$

In the case of non-linear regression, the illuminance model is generalized to a set of matrices.

Testing the Illuminance

Figure 10:
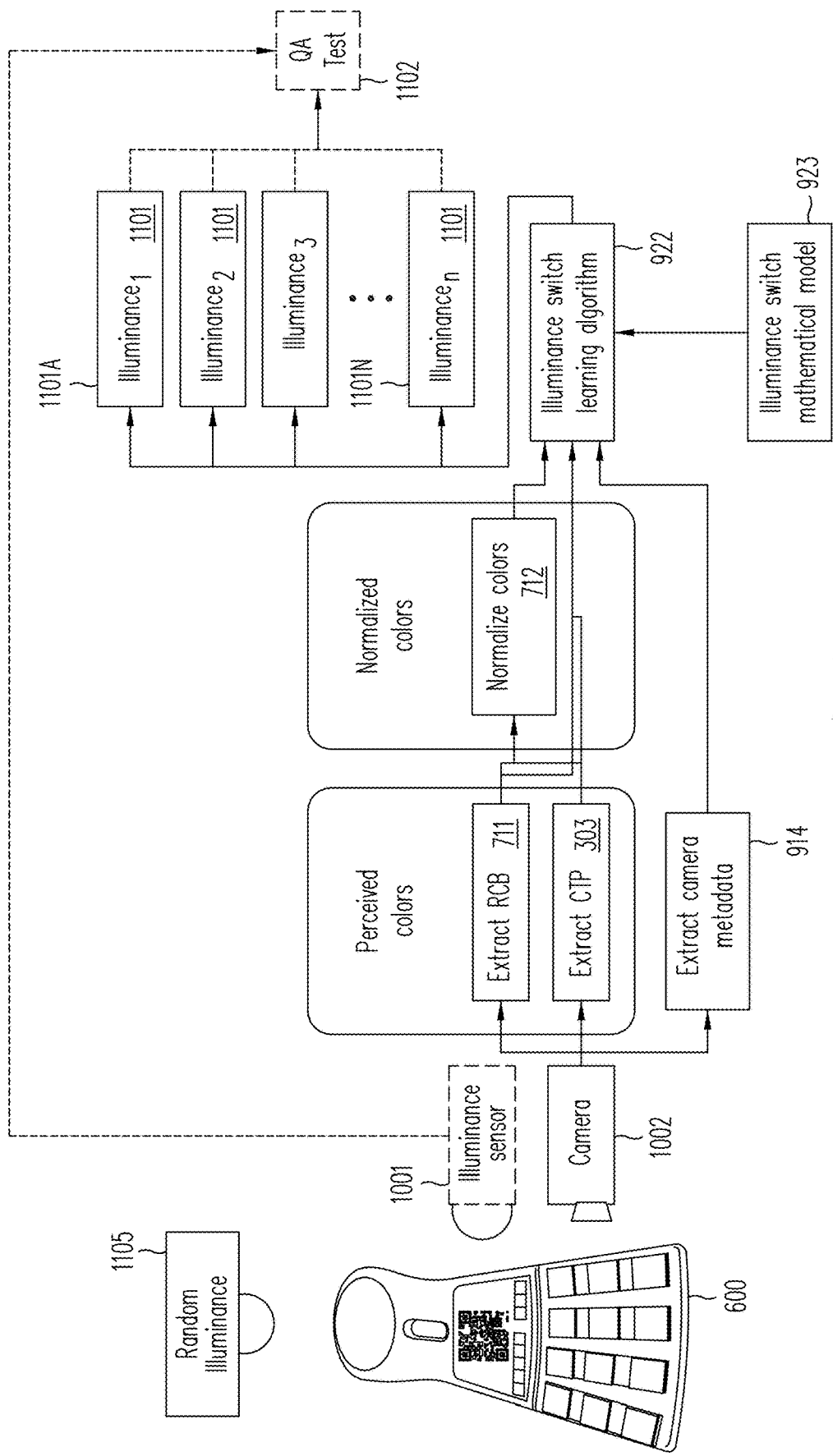
FIG. 10 illustrates a functional block diagram corresponding to the test/QA or measurement phase and the color quantification algorithm of FIG. 7.

Referring now to FIG. 10, the measured vector M determined from the captured picture is entered to test the illuminance model under operation. The illuminance switch mathematical model 923 is used with the parameter vector X that was learned in the learning mode 922. Thus, for a linear regression model, the test/operation for illuminance 1101 is the simple matrix multiplication:

$$M*X=\text{Illuminance}$$

The matrix multiplication allows classifying the illuminance result into one of the n illuminances 1101A-1101N that were used in training the system.

For quality assurance purposes, an illuminance sensor 1001 may be used to obtain a measured value of illuminance. At process block 1102, a quality assurance test may be performed by comparing the measured value of illuminance from the sensor 1001 to the estimated illuminance 1101 predicted by the illuminance model. With this comparison, the accuracy of the learning algorithm and illumination model can be assessed by calculating an average error or a standard deviation from the actual measurements. However, in practice, the illuminance sensor 1001 is typically unavailable.

Data Mining

Machine learning techniques are used to look for cloud separations in points of a database to train a model to discriminate an illuminance level over n illuminance levels. Data mining methods are used on the data captured when taking a plurality of pictures. In one embodiment, data mining techniques analyze all the dimensions of the captured vector M and the dimensions of the metadata vector $M_{Meta}$ to extract parameters for the mathematical illuminance model to determine illuminance in a digital photo when captured.

Figure 13:
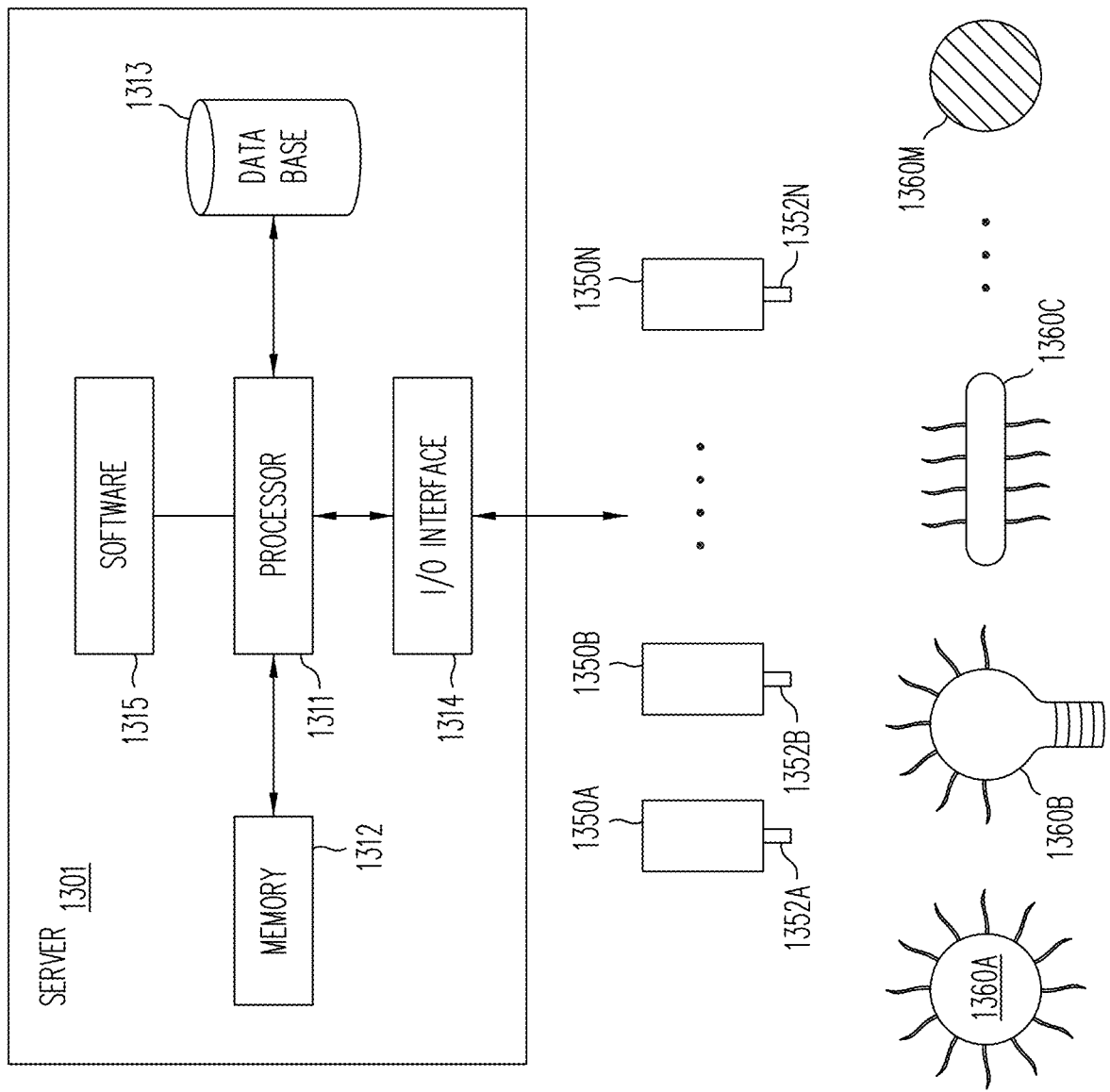
FIG. 13 illustrates a block diagram of a server for data mining a plurality of digital photos stored in a database on a data storage device.

Referring now to FIG. 13, a server 1301 may be used to data mine a database of a plurality of digital photographs. The server 1301 includes a processor 1311, a memory 1312, and one or more storage devices (e.g., hard disk drives) to store instructions of database software and data mining software 1315, and the database 1313 of digital photographs. The processor 1311 executes instructions of the database software and data mining software 1315 to perform the data mining functional processes.

Each of a plurality of portable devices 1350A-1350N (collectively 1350) include digital cameras 1352A-1352N to capture digital photos of a scene that may include a reference color bar and/or chemical test pads. Some of the portable devices may be similar. Other portable devices may differ. The database may take the make and type of digital camera into consideration.

The digital photos may be captured under known differing illuminance values representing a plurality of different lighting conditions 1360A-1360M, from bright sunlight 1360A to dark shadows 1360M, for example. Each portable device 1350 and its camera 1352 may be characterized under every light condition and illuminance value by capturing a digital photo of the same scene. In this manner, the data mining software and server can determine parameters to use for the model to discriminate illuminance in digital photos taken under unknown lighting conditions and illuminance.

Figure 2A:
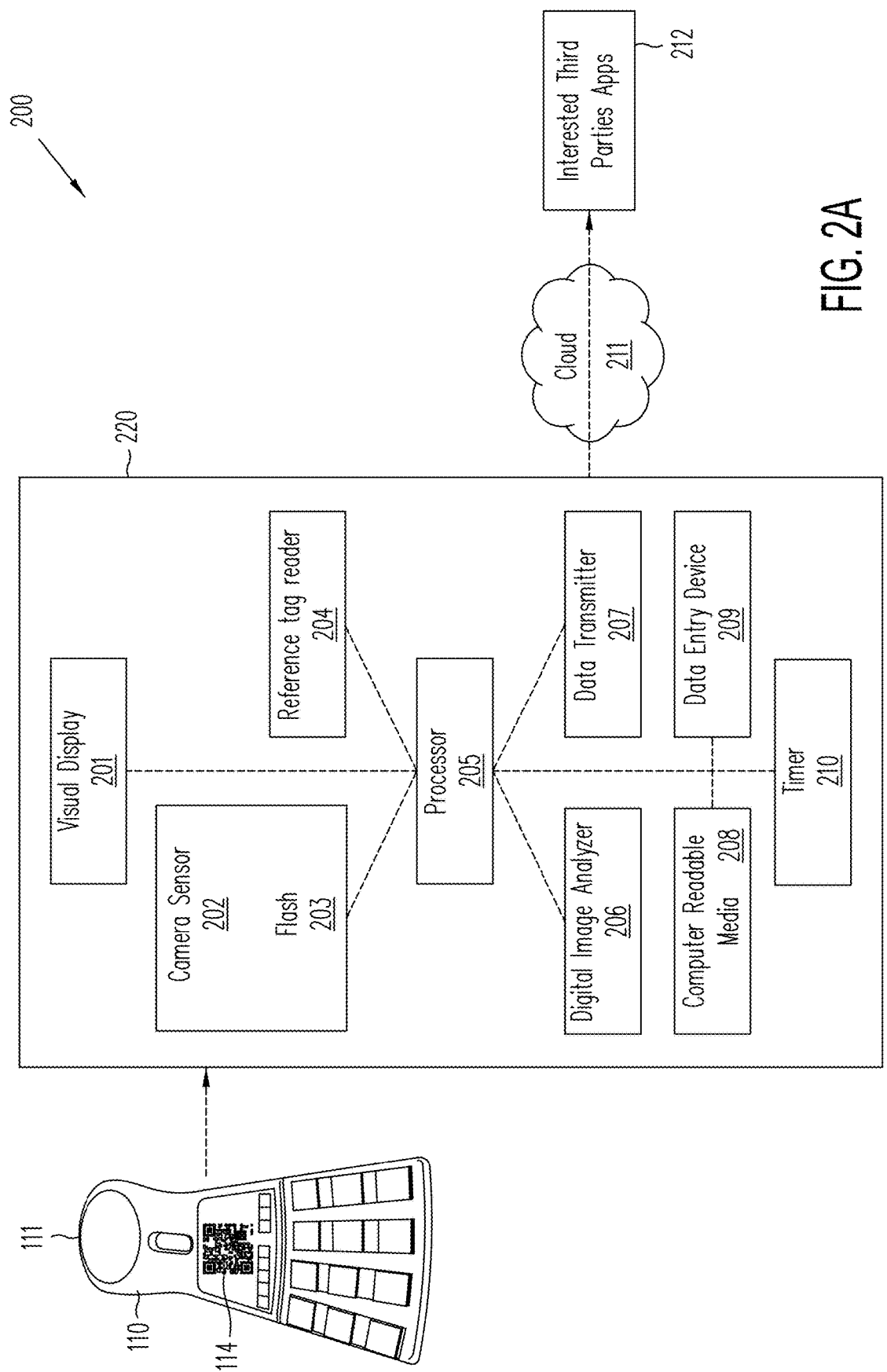
FIG. 2A is a block diagram of a system for analyzing a biological sample of an analysis paddle, according to an embodiment.

The model and the parameters for the model may be stored into a storage device (e.g.,) of a portable device 1350A-1350N for use by a processor, such as the computer readable media 208 for use by the processor 205 of the portable electronic device 220 shown in FIG. 2A. The portable device 1350A-1350N can then capture digital images and discriminate the illuminance under unknown lighting conditions with the model and its parameters. The processor 205 may have additional software instructions in a software application to analyze chemical test pads and determine titrations or concentrations of an analyte in a biological sample applied thereto.

The physical nature of illuminance and the supporting data imposes constraints on the data mining method and the underlying mathematical model. Illuminance is typically a continuous measurement. During image acquisition it is desirable that illuminance be constant or vary slowly. It is desirable that data mining methods be noise-resistant in this continuous environment. The severity of errors may be quantified by the difference between the predicted illuminance and the measured illuminance. The noise resistance and severity of errors can lead towards mathematical methods forming convex partitions in the learning space.

Yet another constraint on the data mining method stems from the use of the training of the illuminance model in an application running on mobile devices. With the application being downloaded, it is desirable that the mathematical model be compact to reduce the download size and the download time. Furthermore, it is desirable that the illuminance model use modest processing resources during the test phase of the algorithm since it is run on mobile devices having constrained resources in both processing power and memory. Moreover, it is desirable to minimize processing time to conserve energy of the mobile device.

Several data mining methods were tested, amongst them all linear methods, including linear regression and linear discriminant analysis, failed to achieve a great accuracy. A naïve Bayesian classification method also failed to reach great accuracy as many parameters of the model were linked therefore violating a Bayesian hypothesis.

Other data mining methods performed well. A tree classification method performed well, providing a compact mathematical model. However, noise resistance was lacking. Additionally, the tree classification method resulted in convex illuminance clusters in the data mining space.

The K nearest neighbor data mining method performed well in terms of accuracy. However, it resulted in convex illuminance clusters in the data mining space. Moreover, its resulting mathematical model is very large due to an enumeration of all the learning samples.

Diagnostic Instruments

The invention relates generally to systems and methods for detecting the presence or absence of a variety of analytes in a fluid sample used with a diagnostic instrument. Diagnostic test results are determined by image analysis of a digital image of the diagnostic instrument. The analysis is performed without the use of any controlling light, such as a flash of light from a camera light source in flash mode, a constant light from the camera light source in torch mode, or any other/additional controlled source light. Rather, the measure of illuminance is determined from existing sensors within digital cameras of personal electronic devices. Moreover, a measure of illuminance can be determined by the embodiments without any external controlled lighting, such as a flash, a torch, or a light emitting diode (LED).

Reagent dipsticks and immunoassays have been used in medical clinics for decades in connection with methods for rapidly diagnosing health conditions at the point of care. In a clinical environment, dipsticks have been used for the diagnosis of urinary tract infections, preeclampsia, proteinuria, dehydration, diabetes, internal bleeding and liver problems. As is known, dipsticks are laminated sheets of paper containing reagents that change color when exposed to an analyte solution. Each reagent test pad on the dipstick is chemically treated with a compound that is known to change color in the presence of particular reactants. For example in the context of urinalysis, the dipstick will typically include reagent pads for detecting or measuring analytes present in a biological sample such as urine or blood, including glucose, bilirubin, ketones, specific gravity, blood type, blood concentration, acidity (pH), protein, urobilirubin (urobilinogen), nitrite (nitrates), leukocytes, microalbumin and creatinin. The magnitude of the color change of the reagent test pad is proportional to the analyte concentration in the patient fluid.

Referring now to FIG. 1A, an example dipstick 101 and an example color reference chart or color interpretation chart 103 are shown. The color interpretation chart 103 is used to make a direct color comparison with a dipstick 101 that has been exposed to a body fluid, such as urine or blood for example. The color interpretation chart 103 is related to the dipstick 101, often being assembled together by the same manufacturer, and thus may be referred to as a Manufacturer Interpretation Color Chart (MICC) 103.

Dipsticks 101 are typically interpreted with a user's naked eye by comparing the test strip 101 against a color reference chart 103. A dipstick reagent color 102 is compared to a set of possible colors 104 corresponding to possible concentrations/titrations/quantity of the tested reagent. However, such color comparison can cause user confusion and error, for several reasons including changes in ambient lighting, and that a significant portion of the population has impaired color vision.

Automatic methods and apparatus for interpreting test results of dipsticks and immunoassays, which have been exposed to a sample solution, are known in the art. One of the approaches is to build a dedicated machine taking the samples into a controlled environment where sensors read the dipsticks illuminated by known light sources. Another approach is to use a camera to capture side by side the dipsticks and a Manufacturer Interpretation Color Chart (MICC) to make a direct color comparison, since test and result interpretation charts are seen under the same lighting. Our approach described in '842 application puts the least constraints on the end-user, as it configures and automatically calibrates the digital image to spectrally correct for any color deficiencies, artifacts, or other ambiguities.

Some embodiments of the invention are drawn to diagnostic instruments, systems and methods of use thereof for testing of a patient fluid sample, which can be used either in clinical settings or for home use. More particularly, embodiments of the invention relate to the performance of color-based reaction testing of biological material in an automatically calibrated environment. In some embodiments, the invention is implemented as an application running on a portable electronic device, such as a cell phone, tablet PC, computer, laptop, a head-mounted display like 'glasses' or other dedicated electronic device. The method has been designed to minimize user contact and manipulations of biologically soiled samples.

With reference to FIG. 1B, a diagnostic instrument 110 is introduced. It is made of a paddle 111 that is populated with the dipstick reagent color 112 and a unique identification tag 114. In response to the tag 114, a map links the reagent types 112 to locations on the paddle 111. The diagnostic instrument could be interpreted manually with a MICC 103. However, with a digital camera of a portable electronic device, colors of exposed reagent types 112 can be automatically interpreted with color quantification methods and algorithms.

In FIG. 2A, a system 200 for diagnosing a patient condition includes the diagnostic instrument 110 and a portable electronic device 220. Generally, the portable electronic device 220 of the system 200 acquires image data of diagnostic instrument 110. The portable electronic device 220 is used for evaluating, analyzing, processing, and/or presenting the image data of diagnostic instrument 110. The system 200 may be used in any type of medical analytical/diagnostic setting, including a medical clinic, an off-site laboratory, or in home without medical supervision.

In certain non-limiting embodiments, the portable electronic device 220 includes a camera sensor 202, a flash or lighting device 203 (e.g., one or more light emitting diodes or a xenon flash bulb), a processor 205, computer-readable media 208, a reference tag reader 204, a visual display device 201, a digital image analyzer 206, a data transmitter 207, a date entry device 209, and a timer 210.

The camera sensor 202 obtains the digital image of the diagnostic instrument 110. The processor 205 is configured to execute program instructions stored on computer-readable media 208 associated with the portable electronic device 220.

The computer-readable media 208 may include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by an electronic device, such as the portable electronic device 220 and its processor 205.

In addition to storing the program for controlling functions of the portable electronic device 220, the computer-readable media 208 may also store data including one or more tables of colors for one or more MICC charts 103 that may be used for comparison to determine test results of the diagnostic instrument 110.

The data transmitter 207 is for transmission of data and information from the portable electronic device 220 to an external electronic device, a computer or server in a computer network, and/or a digital storage device, collectively referred to as a network environment (also referred to as "the cloud") 211. Once the data is provided to the network environment 211, it may be made available to third party applications 212 and used by caregivers, doctors, payment organizations, insurance and health maintenance organizations, pharmacists, or public health organizations.

Figure 2B:
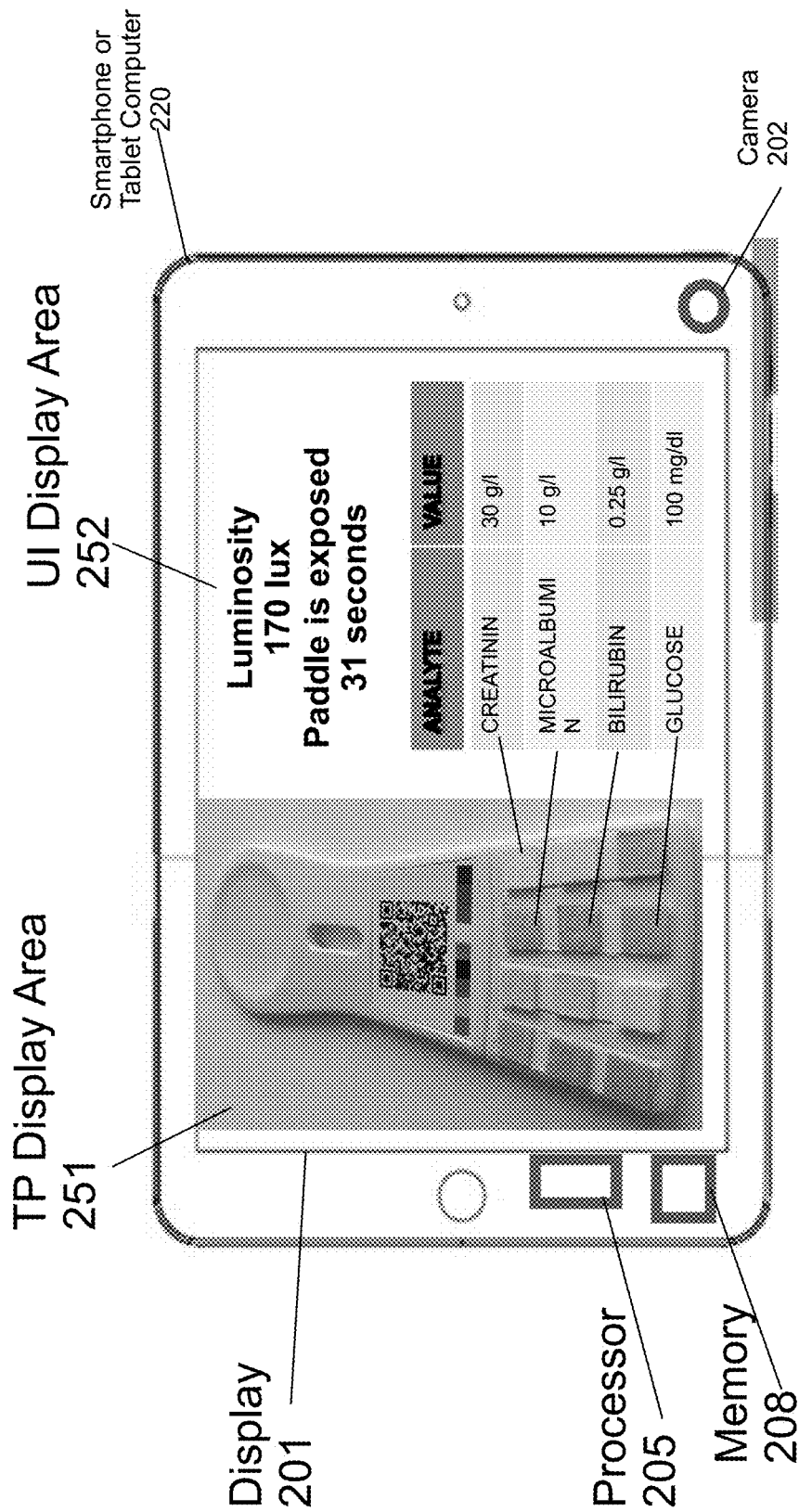
FIG. 2B is an exemplary electronic device of the system for analyzing biological samples.

In FIG. 2B, a smartphone or tablet computer 220 may be used with the diagnostic paddle 110 to obtain results. The smartphone or tablet computer 220 includes a camera 202 and a display device 201 that may be used to obtain and display results from the diagnostic paddle 110. The display device 201 may provide a test paddle (TP) display area 251 to display the test paddle 110 and a user interface (UI) display area 252 to display instructions and results to the user. The smartphone or tablet computer 220 further includes a processor 205 and a memory 208 to store instructions for execution by the processor. The instructions may be software that provide the user interface in the UI display area 252, capture images for display in the display area 251, and perform the algorithms and the methods described herein to obtain the test results.

Referring back to FIG. 1B, the diagnostic instrument 110 is made of a paddle 111, an ID tag 114 and a set of chemical reaction pads or chemical test pads (CTP) 112. The ID tag 114 allows a unique identification and storage of information such as lot number, expiration date, legal mentions etc. associated with the diagnostic instrument. The set of chemical reaction test pads (CTP) 112 perform the tests of the diagnostic instrument. The position of each of the CTP 112 corresponds to a precise test of a biological sample, such as glucose, bilirubin, ketones, specific gravity, blood, pH, etc.

Figure 3A:
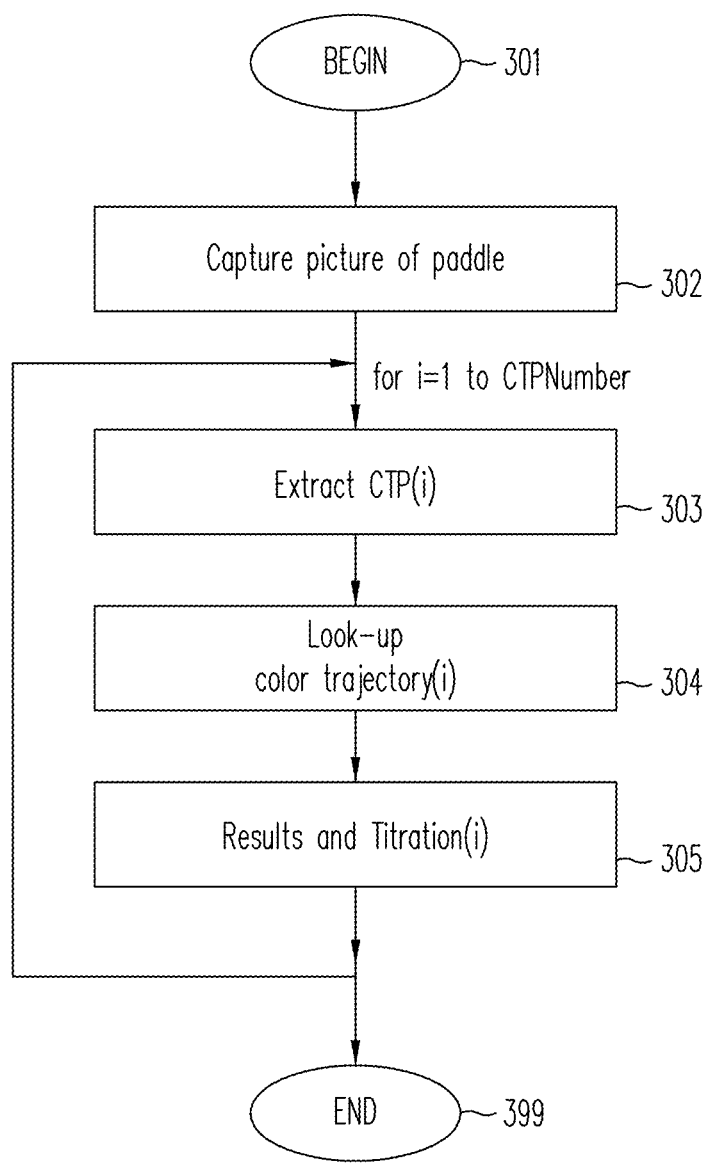
FIG. 3A is a flow chart of a method of color quantification under controlled illuminance.
Figure 3B:
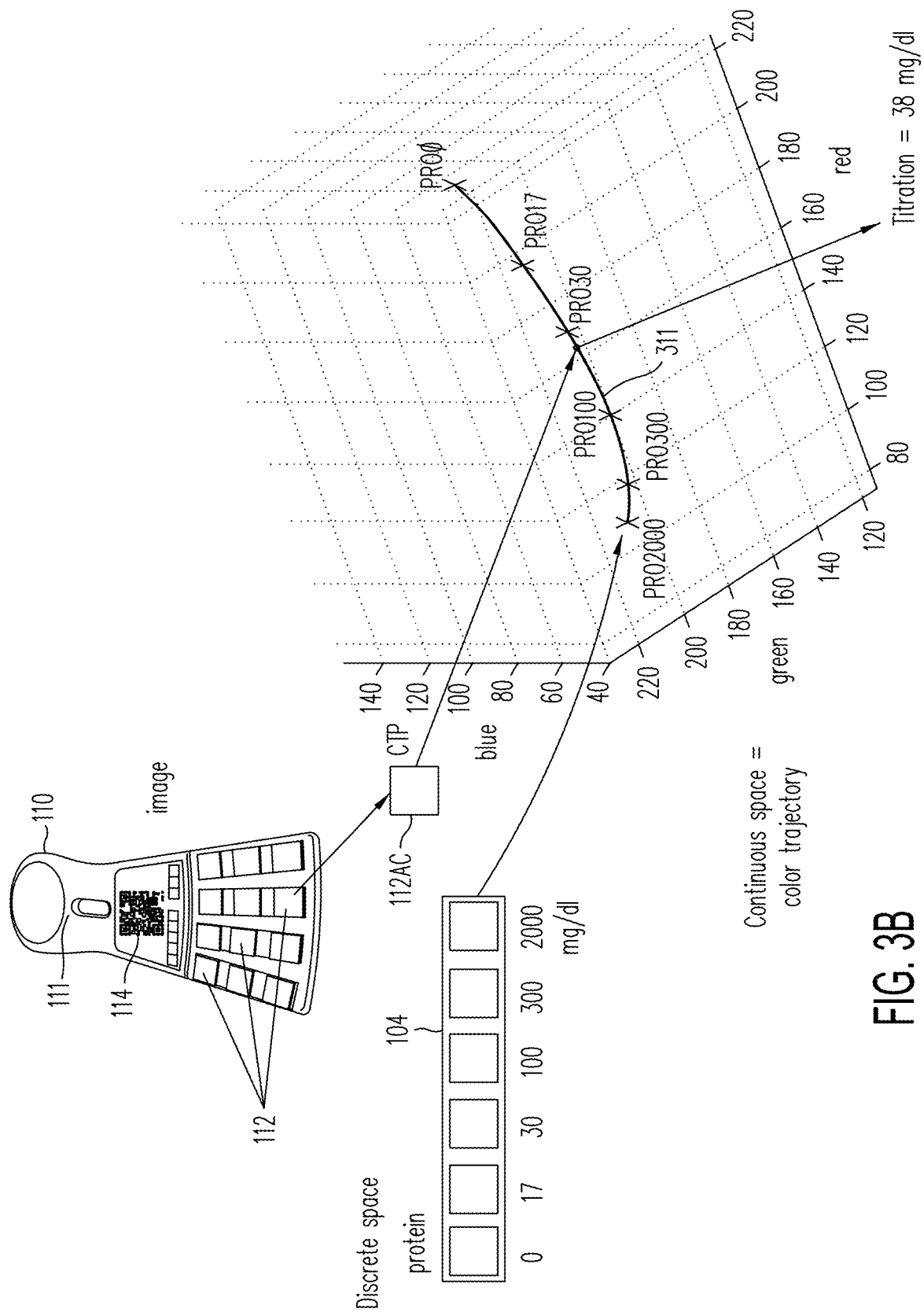
FIG. 3B is a graph illustrating color quantification using a single color trajectory under controlled lighting conditions.

Reference is now made to FIGS. 3A-3B. In FIG. 3A, a flow chart of a method for obtaining diagnostic results from the diagnostic instrument 110 is shown. The process begins at block 301.

At process block 301, the user initiates the method by pressing a button on the display screen 201 of the portable electronic device 220 so that the processor 205 executes a program. The user exposes the set of CTPs 112 of the diagnostic instrument 110 to a biological sample. The analytes contained in the biological sample start a chemical reaction in the CTPs 112 triggering their color change. In certain embodiments, a timer 210 of the portable device 220 is started when the diagnostic instrument 110 is exposed to the biological sample. After a predetermined time passes as may be measured by a clock or timer, such as timer 210 of the device 220, the portable electronic device 220 prompts the user to capture one or more digital images of the diagnostic instrument 110.

At process block 302, a digital image of the diagnostic instrument 110 is captured using the camera sensor of a portable electronic device 220. The captured digital image includes at least the CTPs, and the ID tag of the diagnostic instrument. If included on the diagnostic instrument, the captured digital image may also include a reference color bar.

At process block 303, the position and color of one or more of the CTP 102 are then extracted from the captured digital image of the diagnostic instrument 110. The position of each CTP 112 is then mapped to the type of test it performs (e.g. glucose, acidity (pH)) according to a predetermined map of the set of test pads. Each of these tests can be interpreted by comparing the CTP color to a line of reference colors 104 in the Manufacturer Interpretation Color Chart 103. A line of reference colors 104 represents the color trajectory in the RGB space that a specific chemical test pad follows when submitted to all possible concentrations/titrations/quantity in its detection range. U.S. patent application No. 61/680,842 discloses a continuous trajectory linking all points of the discrete MICC color line 104 of a given analyte to increase accuracy of color quantification. The color trajectories 311 are constructed once, during the calibration procedure of the instrument. The trajectories are formed under known lighting conditions, typically under a lightbox. The color trajectories 311 are stored as look up tables into memory of the device 220 and recalled by the processor to interpret the color of a CTP 112.

At process block 304, under the same known lighting conditions so correction is unnecessary, a color interpretation of the color of the CTP 112 can be made with a simple look-up mechanism by the processor. The look up mechanism maps the values of the camera-captured CTP colors to the nearest point in the corresponding color trajectory 311 of the given analyte of the CTP. The results or titration is directly read out from the trajectory given the camera captured CTP color. There is a one-to-one mapping between a point on the color trajectory 311 and a titration or concentration of analyte in a biological sample.

At process block 305, the result and the titration are reported to a user by the device 220.

The processes 303-305 are repeated for each CTP numbering from i equal to one to a maximum CTP number N. A result and titration (i) is provided for each CTP (i). For the exemplary diagnostic instrument 110, twelve CTPs are analyzed for test results and titration. However, other implementations of diagnostic device 110 may have a different number of CTPs 112.

At process block 399, after all the CTPs of a diagnostic instrument have been color quantified and interpreted to a quantity (e.g., concentration/titration), the process ends.

The color quantification method shown in FIG. 3B works well under known controlled lighting conditions and illuminance, such as a light box at 1600 Lux for example. Additional details of a color quantification method are described in U.S. patent application No. 61/680,842 that is incorporated herein by reference.

However, it is desirable for a color quantification method and system to function over a large range of lighting conditions. Color corrections can be automatically introduced to normalize the extracted colors from the CTPs to the lighting conditions and then comparisons can be performed in this automatically calibrated color space. Experiments have shown that illuminance influences the color trajectories 311 of analytes beyond the effect of the color corrections.

Figure 4:
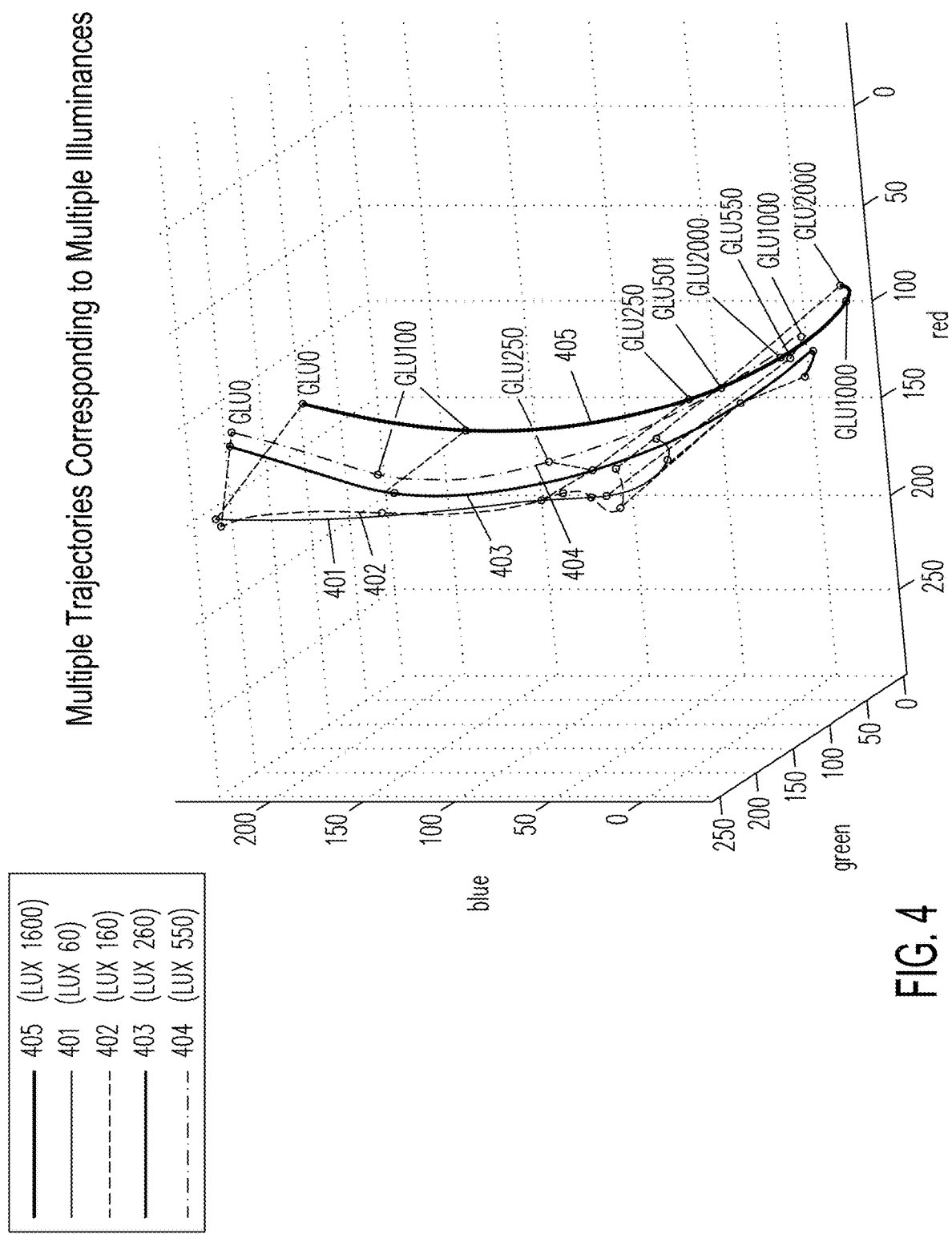
FIG. 4 is a graph of color trajectories for a plurality of different lighting conditions and illuminances.

FIG. 4 illustrates a plurality of MICC color trajectories 401-405 when observing the same CTP (e.g., a Glucose CTP) under several different illuminance conditions. Under bright lighting conditions of 1600 Lux, the color trajectory 405 shows the different colors for the given CTP over the varying concentrations/titrations. For example, the CTP may have a zero analyte concentration at an RGB of approximately 95,184,172 for the illuminance of 1600 lux on trajectory 405. The CTP may have a maximum analyte concentration at an RGB of approximately 86, 29, −37 for the illuminance of 1600 lux on trajectory 405. The color trajectory curve 405 provides good system performance at an illuminance of 1600 Lux, such as may be expected in lighting conditions of an office or a studio, for example. However in dimmer lighting conditions, the 1600 lux color trajectory 405 is not optimal to use in making color comparisons with an extracted color from a CTP.

Additional color trajectories 401-404 were experimentally formed with lower illuminance to extend the operating range of the device 220 to low lighting conditions, such as may be found in corridors, bathrooms, living rooms, kitchens, etc. Color trajectories 401, 402, 403, and 404 were formed corresponding to analyte (e.g., glucose) concentrations/titrations observed under illuminances of 60, 160, 260, and 550 lux respectively. Alternatively, the 1600 lux color trajectory may be mapped to the color trajectories 401-404 respectively for illuminances of 60, 160, 260, and 550 lux by a mapping algorithm.

While only five color trajectories corresponding to analyte (e.g., glucose) concentrations extracted under five different illuminances (e.g., 60, 160, 260, 550, and 1600 lux) are shown in FIG. 4, the embodiments are not to be limited to this number of illuminances and color trajectories. Additional color trajectories for each reagent and test may be formed for other illuminances, where each illuminance level generates its own color trajectory curve. Generally, there is a variance in the color of a CTP under different lighting conditions that is taken into account to acquire a more accurate titration level.

General Color Quantification Algorithm

The method of color quantification shown in FIG. 3A may be adapted to a large range of lighting conditions that may be captured using off-the-shelf cellular phone cameras.

Figure 5:
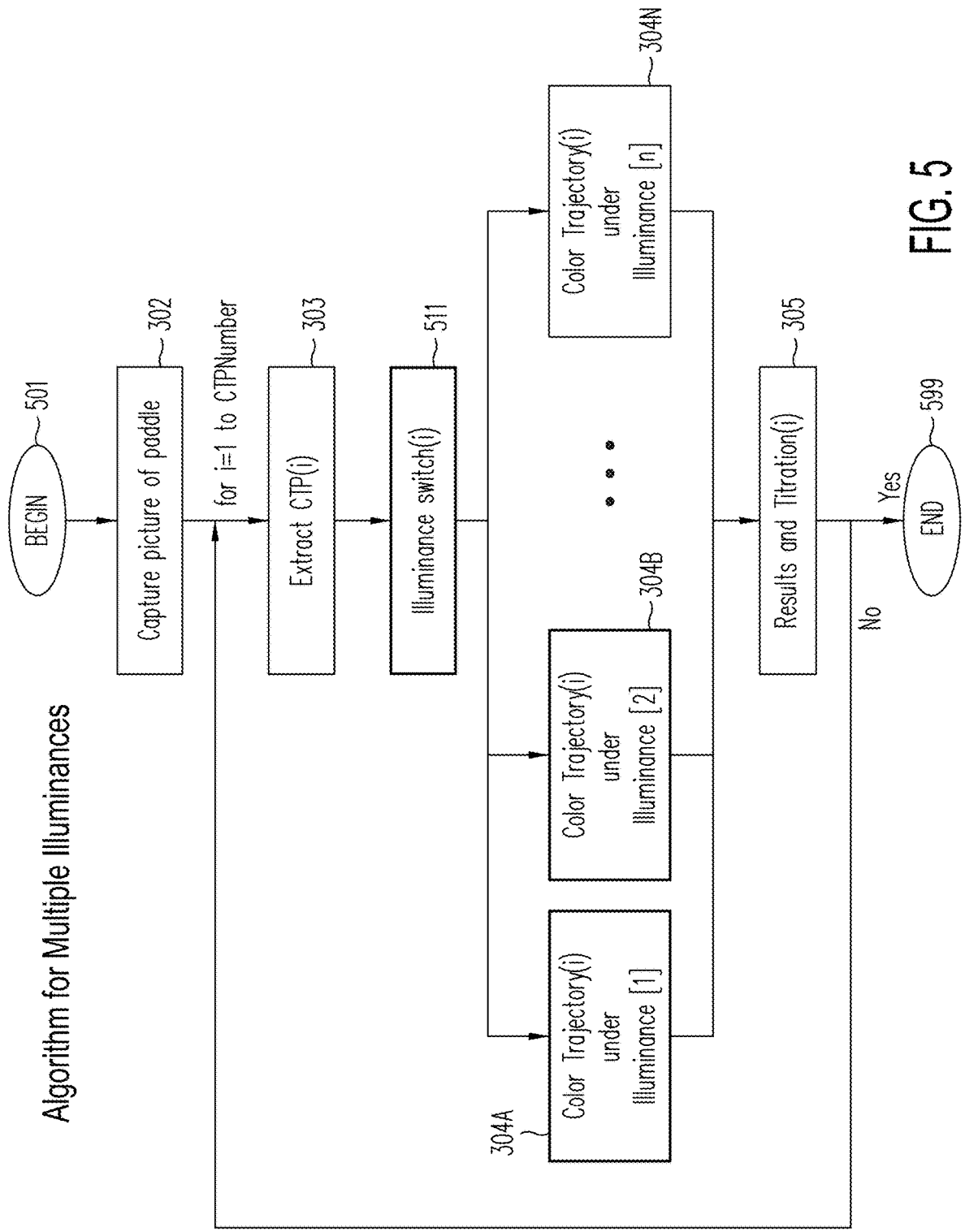
FIG. 5 is a flow chart of a method of color quantification under unknown illuminances.

In FIG. 5, a process 511 is added over those shown in FIG. 3A. At process 511, the illuminance of the diagnostic instrument 110 is estimated based on its acquired picture. This estimated value of illuminance is used to select the proper color trajectory from the plurality of color trajectories 304A-304N to provide accurate color interpretation results.

In one embodiment, there may be five color trajectories 304A-304E corresponding to illuminances of 60, 160, 260, 550 and 1600 Lux. The multiple color trajectories 304A-304E represent the various lighting conditions that may be found inside dwellings, ranging from 60 lux for a poorly lighted environment (e.g., a corridor/closet) to 1600 lux for a well lighted environment (e.g., an office with one or more windows).

After one of the trajectory curves is selected in response to the estimated illuminance, the RGB components of the color are interpreted on the trajectory curve into an analyte concentration/titration. The interpretation is performed by a look up table with the RGB components being the entry points into the table.

At process 305, the results and titration of each CTP are presented to the user. The determined illuminance level may also be presented to the user as part of the results and titration.

Processes 302, 303, and 306 are similar to those described with reference to FIG. 3A.

Figure 6:
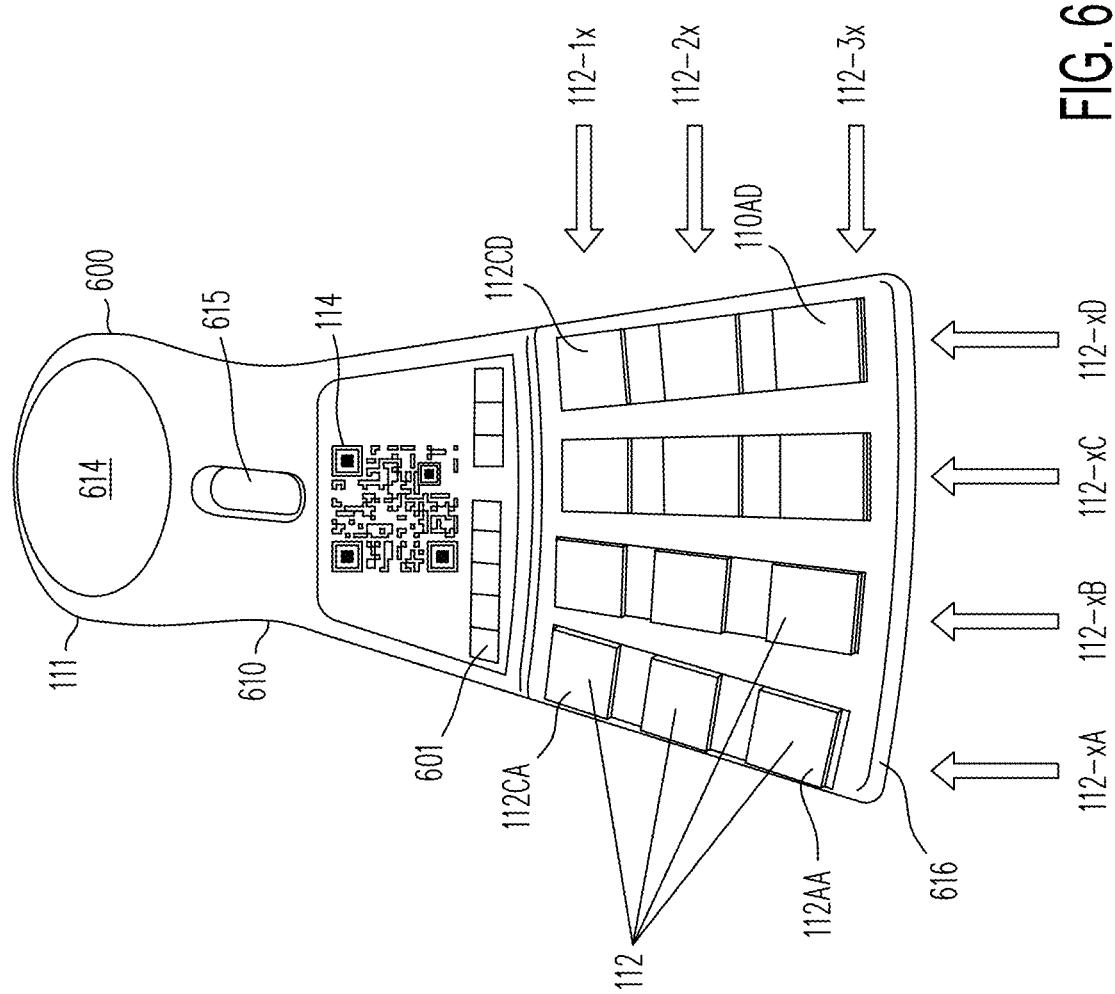
FIG. 6 is an illustration of a diagnostic instrument with a reference color bar (RCB) for illuminance measurements.

The processes of FIG. 5 are repeated for each CTP of the diagnostic instrument (e.g., diagnostic instrument 600 shown in FIG. 6). After all CTPs of the diagnostic instrument have been considered, the process goes to process block 599 and ends.

Estimating illuminance for the accuracy and reliability of a medical device is challenging, especially when using built-in digital cameras of portable electronic devices. Most digital cameras prohibit direct access to their light sensors. Additionally, raw illuminance measurements by the light sensors are manufacturer dependent and largely unspecified. Thus, it is difficult to use the raw illuminance measurements from the light sensors over a wide range of families of devices from different manufacturers. Moreover, manufacturers may regularly announce new devices 220 during the year, such that any luxmeter software application may need regular updates to follow the evolution of new devices. Accordingly it may be desirable to avoid using the light sensors that provide raw illuminance measurements. Instead, the embodiments can estimate illuminance based on the captured image content and basic metadata collected by cameras. Accordingly, new visual clues are introduced into the diagnostic instrument 110 to assist in the estimation of illuminance.

Referring now to FIG. 6, a diagnostic instrument 600 is shown with such new visual clues. The diagnostic instrument 600, also referred to as a test paddle, includes a color reference bar or reference color bar (RCB) 601 adjacent the reagent or chemical test pads 112. The reference color bar (RCB) 601 provides visual color clues on the test paddle 600 to assist in the estimation of illuminance, such as normalizing or correcting colors of the chemical test pads, under different lighting conditions. In some embodiments, the colors of reference color bar (RCB) 601 represent the nominal colors of the CTPs at one or more target concentrations in a biological sample.

The test paddle 600 further comprises a substrate 610 with a handle 614 at one end and a blade 616 at an opposite end. The set 620 of reagent test pads 112 are mounted to the blade portion 616 of the substrate 610 with an adhesive. The substrate may be plastic or a heavy duty paper, such as cardboard.

In one embodiment, the test paddle 600 has twelve reagent pads 112. The twelve reagent pads 112, also referred to as chemical test pads (CTP) or simply test pads, are positioned near the blade of the paddle 600. In this exemplary embodiment, the CTPs 112 are arranged into an array of three rows (112-1$x$ through 112-3$x$) and four columns (112-$x$A through 112-$x$D). Different arrays of CTPs may be used with differing numbers of CTPs on the test paddle.

Each CTP 112 may be treated with a chemical compound (a reagent) specifically selected to react with a specific analyte within a biological sample. Other CTPs may be treated with another chemical compound (reagent) to determine other factors about the biological sample, such as acidity (PH) or specific gravity for example.

Between the handle and the reagent test pads 112 is the reference color bar (RCB) 601. The test paddle 600 may further include a matrix bar code or a two-dimensional bar code 114. The test paddle 600 may further include an opening 615 capable of hosting an additional test, such as a pregnancy test.

The reference color bar 601 includes a plurality of color samples in a side-by-side linear arrangement. For example, the reference color bar 601 may include color samples for one or more of the following colors: Cyan, Magenta, Yellow, Key (black), Gray, White, Red, Green, Blue. The sample colors correspond with common color spaces, such as Red-Green-Blue or Cyan-Magenta-Yellow-Key (black). The known color samples may be shaped as color squares along the reference color bar or alternatively other two dimensional shapes such as color circles, color ovals, or color rectangles.

The reference color bar 601 is used for image processing. The RCB 601 may be used to calibrate or normalize a digital image of the diagnostic instrument to improve the quality and accuracy of color analysis. Additionally, the reference color bar 601 may be used to determine the illuminance. The reference color bar (RCB) 601 may be used to automatically correct the captured colors of the different reagent test pads 112, prior to a comparison with a set of color calibration curves to determine analyte concentration in the test sample. The new visual clues provided by the reference color bar 601 on the test paddle 600 lead to an improved flow chart for color quantification.

The matrix bar code or two-dimensional bar code 114 may also referred to as a quick response (QR) code 114, The quick response (QR) code 114 can provide a unique identification to automatically identify the test paddle 600. The QR code 114 may be configured to contain certain identification information about the test paddle 600, such as a list of the analytes that are being tested, expiration date of the paddle 600, the conditions that are being tested, and other identifying information. The information may be printed directly on the unique identification or encrypted within the QR code 114.

Alternatively, the QR code 114 may be associated with information stored elsewhere, such as is the case with bar codes or other near-field communication codes. The identification information may be used in a validation processes to ensure the diagnostic test paddle 600 is suitable for the tests being performed and to ensure that it is safe to use, in good working condition, or to resolve other issues which may impact quality and reliability of the test results.

Figure 7:
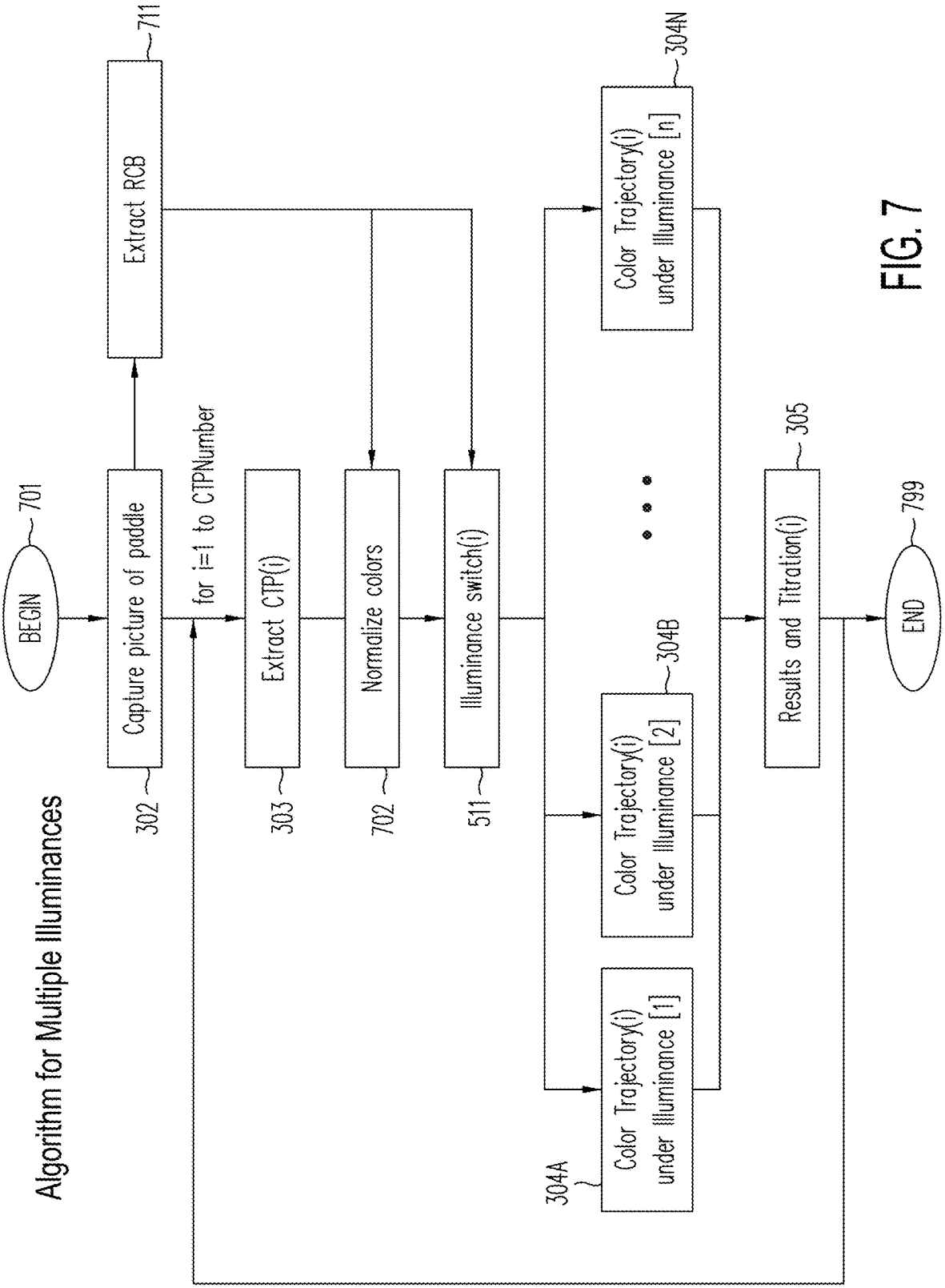
FIG. 7 is a flow chart of a method of color quantification including the processing of the image of the reference color bar chart (RCB)

Referring now to FIG. 7, a flow chart illustrates a method of color quantification including the processing of the image of the reference color bar chart (RCB). The method starts at block 701 and goes to process block 302.

Processes 302, 303, 305, and 306 are similar to those described with reference to FIG. 3A. Process 511 and selection of one of the trajectories 304A-304N is similar to that described with reference to FIG. 5. The method illustrated by FIG. 7 introduces process blocks 711 and 702 to that of FIG. 5. The processes of FIG. 7 are repeated for each CTP of the diagnostic instrument. After all CTPs have been considered, the process goes to process block 799 and ends.

At process block 711, RGB color values for the reference colors of the reference color bar 601 are extracted from the captured picture of the diagnostic instrument 600. The reference color bar values are used to make two kinds of corrections at process blocks 702 and 511.

At process block 702, a color normalization process occurs. The color normalization process transforms the perceived colors from each CTP into a normalized color space. This operation calculates the inverse transform to be applied to the perceived RCB colors so that these colors appear as seen under a normalized lighting environment, e.g. D65. This inverse transform is then applied to the perceived RGB colors of the CTP to determine their normalized color. The normalized RGB colors for each CTP are used to determine the concentration/titration using a selected color trajectory. The normalization process is further described in U.S. Patent Application No. 61/973,208 and incorporated herein by reference.

At process block 511, an illuminance correction is made with the reference colors of the reference color bar. The RCB colors of the reference color bar are used in the illuminance switch process 511, in conjunction with other parameters like the camera metadata and CTP colors, to make a high precision luxmeter determination of the illuminance of the paddle.

Dimension of the Illuminance Switch Problem Space

Camera metadata may be some of the parameters that may be used by the illuminance model. Camera metadata for photograph i may be expressed in vector form by an $M_{Meta}$ vector (meta vector) as follows:

$$M_{Meta\ i}=[\text{ExposureTime}_i\ \text{ShutterSpeed}_i\ F\text{Number}_i\\ \text{Aperture}_i\ \text{Brightness}_i\ \text{IsoSpeedRating}_i]$$

Camera metadata of a photograph are insufficient to accurately measure illuminance. Additional data that extends the model is used to accurately measure illuminance of a scene. The referenced color bar (RCB) 601 is introduced into the captured scene of the photograph to more accurately measure illuminance. The test paddle 600 further includes the chemical test pads 112 that are captured in the photograph that may also be used to more accurately measure illuminance.

For the reference color bar (RCB) 601, a new observation vector corresponding to the RGB colors of the sample colors—Cyan, Magenta, Yellow, Key (black), Gray, White, Red, Green, Blue—of the RCB 601 is introduced and used in the model. The new observation vector $M_{percRCB\ i}$ has a dimension 27 (3 RGB×9 colors) and is as follows:

$$M_{percRCB\ i}=[p\text{Cyan}_{R\ i}\ p\text{Cyan}_{G\ i}\ p\text{Cyan}_{Bi}\ldots p\text{Blue}_{R\ i}\\ p\text{Blue}_{G\ i}\ p\text{Blue}_{B\ i}]$$

The observation vector of the reference color bar may also be normalized and used in the model. A normalized RCB adds another line vector $M_{normRCB\ i}$ (normalized reference color bar vector) into the model with the same dimension 27 as follows:

$$M_{normRCB\ i}=[n\text{Cyan}_{R\ i}\ n\text{Cyan}_{G\ i}\ n\text{Cyan}_{Bi}\ldots n\text{Blue}_{R\ i}\\ n\text{Blue}_{G\ i}\ n\text{Blue}_{B\ i}]$$

While the new observation vector mentioned above is based on known RGB sample colors, different numbers and combinations of known reference colors may be used. In one embodiment, the reference colors of the RCB are nominal colors of each CTP at one or more, or all predetermined target concentrations.

The observed or captured scene in the digital photograph includes the CTPs 112 of the test paddle 600. In one embodiment there are twelve CTPs 112, CTP1 through CTP12, each of which is captured with the three red, green, and blue (RGB) color values. With twelve CTPs, the corresponding line vector $M_{percTPi}$ that is captured for a test paddle has a dimension 36:

$$M_{percCTP\ i}=[p\text{CTP1}_{R\ i}\ p\text{CTP1}_{G\ i}\ p\text{CTP1}_{Bi}\ldots\\ p\text{CTP12}_{R\ i}\ p\text{CTP12}_{G\ i}\ p\text{CTP12}_{B\ i}]$$

The measured or observation vector of the CTPs may also be normalized and used in the model. A normalized CTP vector adds another line vector $M_{normCTP\ i}$ into the model with the same dimension 36:

$$M_{normCTP\ i} = [nCTP1_{R\ i}\ nCTP1_{G\ i}\ nCTP1_{Bi} \ldots nCTP12_{R\ i}\ nCTP12_{G\ i}\ nCTP12_{B\ i}]$$

The reference color bar RCB vectors and the CTP vectors can be combined together into a single line vector. For a given photograph i, the RCB and CTP vectors combine into a single $M_{RCBCTP}$ vector of dimension 126:

$$M_{RCBCTP\ i} = [M_{percRCB\ i}\ M_{normRCB\ i}\ M_{percCTP\ i}\ M_{normCTP\ i}]$$

Despite the high dimension of elements in the $M_{RCBCTP}$ vector, determining illuminance of a test paddle is still a challenge. Variables in the $M_{RCBCTP}$ vector were analyzed to determine their use in classifying images according to their illuminance. Of the 126 dimensions corresponding to the RGB representations of all the points (CTP+RCB) in the $M_{RCBCTP}$ vector, there was no single dimension or combination of dimensions found that could separate points and discriminate illuminance from different lighting conditions. Accordingly, the added six dimensions of metadata are used to look for cloud separations in 132 dimensions of problem space. With so many dimensions, machine learning techniques are useful to look for cloud separations in points and discriminate illuminance.

Accordingly, data mining methods were introduced that work over all of the data captured when taking a plurality of pictures. In one embodiment, data mining techniques include, but are not limited to, the one hundred twenty six (126) dimensions of the captured vector $M_{RCBCTP}$, and the six (6) dimensions of the metadata vector $M_{Meta}$, for a total of 132 dimensions in accordance with one embodiment to form a vector $M_i$.

$$M_i = [M_{RCBCTP\ i}\ M_{Meta\ i}]$$

size($M_i$)=(1, 132) in one embodiment

Learning the Illuminance Switch

Figure 8:
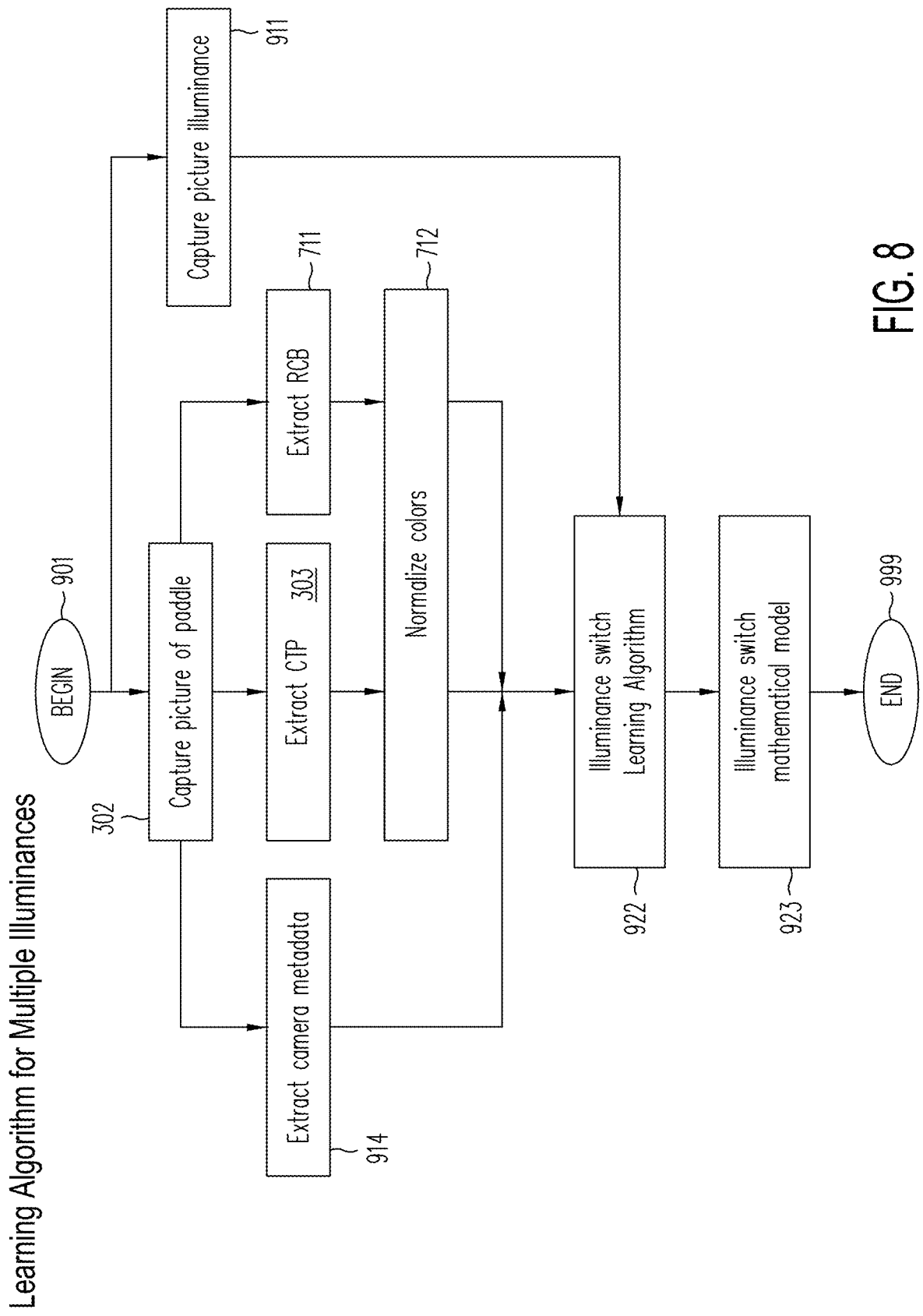
FIG. 8 illustrates a flow chart of a learning algorithm during a learning phase to acquire a mathematical model of the illuminance switch.

Reference is now made to FIGS. 8-9. FIG. 8 illustrates a flow chart of the learning method for the illuminance model. FIG. 9 is a block diagram illustrating how the method is used with the illuminance model in the experimental learning setting. The learning environment performs tests under controlled lighting, with illuminance 1005 set to one of the n buckets of illuminance [1 . . . n]. The total number of tests q is determined by the acceptable error rate of the learning. For each test, an image is captured simultaneously by the camera 1002 and by the illuminance sensor 1001. The method begins at process block 901 and then goes to process blocks 302 and 911 which may be performed concurrently in parallel.

At process block 911, the illuminance sensor 1001 measures the illuminance Illuminance$_i$ at the diagnostic instrument 600. The measurement of illuminance is coupled to the process block 922.

At process block 302, a camera 1002 concurrently captures a photograph or picture, a digital image of the diagnostic instrument 600 (also referred to as a test paddle). The process then goes to process blocks 303, 711, and 914 that can be concurrently performed in parallel.

At process block 303, the perceived colors of the CTPs are extracted from the captured photograph of the instrument 600.

At process block 711, the perceived colors of the RCB are extracted from the captured photograph of the instrument 600.

At process block 914, the camera metadata associated with the captured photograph of the instrument 600 is extracted from the captured photograph. The process may then go to process block 712.

At process block 712, the perceived CTP and the perceived RCB vectors are normalized to form the corresponding normalized CTP vector and normalized RCB vector. With the perceived RCB vector, the perceived CTP vector, the normalized RCB vector and the normalized CTP vector, the $M_{RCBCTP}$ vector can be constructed which represents one line in the observation vector $M_i$ for the learning matrix. Both $M_i$ and Illuminance$_i$ are entered into the learning algorithm 922, in the following system:

$$\begin{bmatrix} M_1 \\ M_2 \\ \vdots \\ M_q \end{bmatrix} * \begin{bmatrix} X_1 \\ X_2 \\ X_3 \\ \vdots \\ X_m \end{bmatrix} = \begin{bmatrix} \text{Illuminance}_1 \\ \text{Illuminance}_2 \\ \vdots \\ \text{Illuminance}_q \end{bmatrix}$$

During the learning phase, numerous (e.g., hundreds) images are generated for each illuminance [1 . . . n], resulting in several (e.g., thousands) overall tests q. In one embodiment, the dimension m=126+6=132. However, the illuminance model may be used with any dimension of vector. After all tests are performed, the learning algorithm process 922 determines the mathematical model capable of best predicting Illuminance$_x$, based on vector $M_x$.

At process block 922, the illuminance model is formed with a regression model that is capable of classifying the illuminance into n bins in response to the observation vector $M_i$. In the simple case of a linear regression, the illuminance model is trained with the parameter vector X the transpose of which is as follows:

$$X^T = [X_1\ X_2\ X_3 \ldots X_m]$$

In the case of non-linear regression, the illuminance model is generalized to a set of matrixes.

Testing the Illuminance Switch

Reference is now made to FIG. 10. The parameter vector X for the illuminance model has been determined. During the test phase of the illuminance model, hundreds of images are generated by a light source with a random illuminance value 1105, within the range of possible illuminance values. Test images of the diagnostic instrument 600 captured by the camera 1002 are treated independently. Each test image is processed with the illuminance model similar to that of the learning phase and the method illustrated by FIG. 8 but for processes 911,922,923. Usually the illuminance sensor 1001 and the capture illuminance process 911 shown in FIG. 8 are typically unavailable in an operational mode. Instead of a learning mode, processes 922,923 function in an operational mode. To test the operational mode, the illuminance sensor 1001 is used in the capture illuminance process 911 to compare with the predicted illuminance 1101A-1101N.

At process 711, the perceived colors of the RCB are extracted from the picture. At process 303, the perceived colors of the CTPs are extracted from the picture. At process 914, the camera metadata is extracted from the picture. At process 712, the perceived colors of the CTP and RCB are normalized into normalized color CTP and normalized color RCB, respectively. The perceived and normal colors of the CTP and RCB are combined together with the metadata into a measured vector M.

The measured vector M determined from the captured picture is entered to test the illuminance model under operation. The illuminance switch mathematical model 923 is used with the parameter vector X that was learned in the learning mode with the illuminance switch learning algorithm 922. Thus, for a linear regression model, the test/operation for illuminance 1101 is a simple matrix multiplication as follows:

$$M*X=\text{Illuminance}$$

The matrix multiplication allows classifying the illuminance results into one of the n illuminances 1101A-1101N that were used in training the system.

For quality assurance testing purposes, an external illuminance sensor 1001 may be used in parallel with the camera 1002 to obtain a measured value of illuminance when the captured photograph of the diagnostic instrument is taken. At process block 1102, a quality assurance test may be performed by comparing the measured value of illuminance from the sensor 1001 to the estimated illuminance 1101 predicted by the illuminance model. With this comparison, the accuracy of the learning algorithm and illumination model can be assessed by calculating an average error of the measurements and its precision can be assessed by the standard deviation of the measurements. However, in practice, the illuminance sensor 1001 is typically unavailable and the quality assurance testing process 1102 is not performed.

Data Mining

As mentioned herein, machine learning techniques are used to look for cloud separations in points of a database (e.g., hyper planes separating points in the database) to train the model to discriminate illuminance over the n illuminance values to determine the best estimate of illuminance. Data mining methods are used on the data captured when taking a plurality of pictures. In one embodiment, data mining techniques analyze the one hundred twenty six (126) dimensions of the captured vector $M_{RCBCTP}$, and the six (6) dimensions of the metadata vector $M_{Meta}$, to extract parameters for the mathematical illuminance model to discriminate illuminance in a digital photo from the n illuminance values that may be possible.

In one embodiment the data mining algorithm is a quadratic discriminant analysis. It has precise results (e.g., in one case greater than 99.75% correct results), is noise resistant, and relies on a convex mathematical model. Moreover, it produces a compact mathematical model that is moderately processor (CPU) and memory intensive during the test phase, because it just performs matrix multiplication.

The preferred illuminance model transmits a squared matrix of size 132, in addition to 5 vectors of size 132, each of which represents the centroid of an illuminance bucket.

Optionally an additional step of principle component analysis (PCA) can be applied to the data mining algorithms to reduce the size of the mathematical model to be transmitted to the application. In this case, the size of the preferred embodiment can be reduced from a dimension of 132 to 20. The tradeoff is approximately a 1% loss of accuracy (>98.75% correct results) for a reduction of the mathematical model size by a factor of 36.

Other machine learning techniques may be used as well, such as support vector machine (SVM), random forests, neural networks, deep belief networks, and deep Boltzman machines.

CONCLUSION

When implemented in software, the elements of the embodiments of the invention are essentially the code segments or instructions to perform the functional tasks described herein. The code segments or instructions are executable by a processor and can be stored in a storage device or a processor readable storage medium, awaiting execution. The processor readable storage medium may include any medium that can store information. Examples of the processor readable storage medium include an electronic circuit, a semiconductor memory device, a read only memory (ROM), a flash memory, an erasable programmable read only memory (EPROM), a magnetic disk, a floppy diskette, a hard disk, an optical disk, a compact disk read only memory (CD-ROM), and a Blu-ray disk. The code segments or instructions may also be downloaded via computer networks such as the Internet, Intranet, etc. and stored into a storage device or processor readable storage medium and executed by the processor.

While certain embodiments of the disclosure have been described, these embodiments have been presented by way of example only, and are not intended to limit the scope of the disclosure. Various combinations and sub-combinations, and modifications as may be made, of the presently disclosed components and embodiments and aspects are contemplated whether or not specifically disclosed hereunder, to the extent and as would be apparent to one of ordinary skill based upon review of this disclosure and in order to suit a particular intended purpose or application. Indeed, the novel methods, systems, and devices described herein may be embodied in a variety of other forms. Furthermore, various omissions, substitutions and changes in the form of the methods, systems, and devices described herein may be made without departing from the spirit of the disclosure. For example, certain features that are described in this specification in the context of separate implementations may also be implemented in combination in a single implementation. Conversely, various features that are described in the context of a single implementation may also be implemented in multiple implementations, separately or in sub-combination.

Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed invention is to be limited only by patented claims that follow below.

What is claimed is:

1. A diagnostic system for biological samples, the diagnostic system comprising:
   a diagnostic instrument having a reference color bar and a plurality of chemical test pads exposed to receive a biological sample; and
   a portable electronic device including,
      a digital camera configured to capture a digital image of the diagnostic instrument, a processor coupled the digital camera and configured to receive data associated with the digital image, and
      a storage device coupled to the processor, the storage device storing therein multiple color trajectories, wherein each color trajectory is associated with a different value of illuminance and is indicative of color variance that a first chemical test pad of the plurality of chemical test pads tends to exhibit when exposed to different levels of an analyte in the biological sample, and instructions for execution by the processor that when executed cause the processor to:
- extract a color of the first chemical test pad from the received data;
- determine a measure of illuminance associated with the digital image based on the received data;
- select a color trajectory from the multiple color trajectories stored in the storage device based on the determined measure of illuminance; and
- determine a test result based at least in part on color interpretation of the first chemical test pad using the selected color trajectory.

2. The diagnostic system of claim 1, wherein the test result is acidity (PH) of the biological sample.

3. The diagnostic system of claim 1, wherein the biological sample is one of urine or blood.

4. The diagnostic system of claim 1, wherein the test result is one of blood type, an analyte concentration in the biological sample, protein concentration in the biological sample, nitrite concentration in the biological sample, leukocyte concentration in the biological sample, urobilinogen concentration in the biological sample, microalbumin concentration in the biological sample, bilirubin concentration in the biological sample, glucose concentration in the biological sample, ketone concentration in the biological sample, and specific gravity of the biological sample.

5. The diagnostic system of claim 1, wherein the diagnostic instrument further includes an identification tag with information related to the diagnostic instrument stored therein.

6. The diagnostic system of claim 5, wherein the digital image of the diagnostic instrument captured by the digital camera includes an image of the reference color bar, the plurality of chemical test pads, and the identification tag.

7. The diagnostic system of claim 1, wherein the instructions when executed further cause the processor to report the test result to a user.

8. The diagnostic system of claim 1, wherein the instructions when executed further cause the processor to extract a position of the first chemical test pad from the captured digital image.

9. The diagnostic system of claim 8, wherein the instructions when executed further cause the processor to map the extracted position to a type of test to be performed.

10. The diagnostic system of claim 1, wherein the portable electronic device includes a smart phone or a tablet computer.

11. A diagnostic system for biological samples, the diagnostic system comprising:
- a diagnostic instrument having a plurality of chemical test pads configured to receive a biological sample; and
- a portable electronic device including a digital camera configured to capture a digital image of at least the plurality of chemical test pads, a storage device storing multiple color trajectories, wherein each color trajectory is associated with a different value of illuminance and is indicative of color variance that a first chemical test pad of the plurality of chemical test pads tends to exhibit when exposed to different levels of an analyte in the biological sample, and a processor, wherein the processor is configured to:
  - extract a color of the first chemical test pad from the captured digital image;
  - select a color trajectory from the multiple color trajectories stored in the storage device;
  - analyze the extracted color using the selected color trajectory; and
  - determine a test result based on the analysis.

12. The diagnostic system of claim 11, wherein the processor is configured to determine a measure of illuminance associated with the digital image based on the captured digital image.

13. The diagnostic system of claim 11, wherein the diagnostic instrument further includes a reference color bar that is captured in the digital image, wherein the processor determines the measure of illuminance based on data associated with the reference color bar in the digital image.

14. The diagnostic system of claim 13, wherein the processor is configured to select the color trajectory based on the determined measure of illuminance.

15. The diagnostic system of claim 11, wherein the processor is further configured to report the test result to a user.

16. The diagnostic system of claim 11, wherein the portable electronic device includes a smart phone or a tablet computer.

17. The diagnostic system of claim 11, wherein the biological sample is one of urine or blood.

18. The diagnostic system of claim 11, wherein the test result is one of blood type, an analyte concentration in the biological sample, protein concentration in the biological sample, nitrite concentration in the biological sample, leukocyte concentration in the biological sample, urobilinogen concentration in the biological sample, microalbumin concentration in the biological sample, bilirubin concentration in the biological sample, glucose concentration in the biological sample, ketone concentration in the biological sample, and specific gravity of the biological sample.

* * * * *